US010226520B2

(12) United States Patent
Torres

(10) Patent No.: US 10,226,520 B2
(45) Date of Patent: Mar. 12, 2019

(54) **COMPOSITIONS AND METHODS FOR ENTEROHEMORRHAGIC *ESCHERICHIA COLI* (EHEC) VACCINATION**

(71) Applicant: Alfredo G. Torres, Friendswood, TX (US)

(72) Inventor: Alfredo G. Torres, Friendswood, TX (US)

(73) Assignee: THE BOARD OF REGENTS OF THE UNIVERSITY OF TEXA SYSTEM, Austin, TX (US)

( * ) Notice: Subject to any disclaimer, the term of this patent is extended or adjusted under 35 U.S.C. 154(b) by 0 days.

(21) Appl. No.: 15/436,044

(22) Filed: Feb. 17, 2017

(65) Prior Publication Data

US 2017/0189516 A1 Jul. 6, 2017

Related U.S. Application Data

(63) Continuation-in-part of application No. 14/638,956, filed on Mar. 4, 2015, now Pat. No. 9,579,370.

(60) Provisional application No. 61/948,001, filed on Mar. 4, 2014.

(51) Int. Cl.
*A61K 39/00* (2006.01)
*A61K 39/108* (2006.01)

(52) U.S. Cl.
CPC ...... *A61K 39/0258* (2013.01); *A61K 2039/53* (2013.01); *A61K 2039/543* (2013.01); *A61K 2039/545* (2013.01); *A61K 2039/552* (2013.01); *A61K 2039/55594* (2013.01); *A61K 2039/575* (2013.01)

(58) Field of Classification Search
None
See application file for complete search history.

(56) References Cited

U.S. PATENT DOCUMENTS

| | | | | |
|---|---|---|---|---|
| 4,744,984 | A | 5/1988 | Ragland | 424/282.1 |
| 7,300,659 | B2 | 11/2007 | Finlay | 424/234.1 |
| 8,507,249 | B2 | 8/2013 | Finlay | 435/252.3 |
| 2009/0327170 | A1 | 12/2009 | Donati | 706/19 |

FOREIGN PATENT DOCUMENTS

| | | | |
|---|---|---|---|
| JP | 200235507 | A * | 10/2002 |
| WO | WO 98/15578 | | 4/1998 |

OTHER PUBLICATIONS

Google english translation of JP200235507-A.*

Abu-Aii GS, Ouellette LM, Henderson ST, Lacher OW, Riordan JT, Whittam TS, Manning SO. 2010. Increased adherence and expression of virulence genes in a lineage of *Escherchia coli* 0157:H7 commonly associated with human infections. PLoS One 5:e10167.

Amani J, Mousavi SL, Rafati S, Salmanian AH. 2011. Immunogenicity of a plant-derived edible chimeric EspA, Intimin and Tir of *Escherichia coli* 0157:H7 in mice. Plant Sci 180:620-627.

Arthur TM, Ahmed R, Chase-Topping M, Kalchayanand N, Schmidt JW, Bono JL. 2013. Characterization of *Escherichia coli* 0157:h7 strains isolated from supershedding cattle. Appl. Environ Microbial 79:4294-4303.

Babiuk S, Asper DJ, Rogan D, Mutwiri GK, Potter AA. 2008. Subcutaneous and intranasal immunization with type III secreted proteins can prevent colonization and shedding of *Escherichia coli* 0157:H7 in mice. Microb Pathog 45:7-11.

Barat S, Willer Y, Rizos K, Claudi B, Maze A, Schemmer AK, Kirchhoff D, Schmidt A, Burton N. Bumann D. 2012. Immunity to intracellular Salmonella depends on surface-associated antigens. PLoS Pathog 8:e1002966.

Bentancor LV, Bilen M, Brando RJ, Ramos MV, Ferreira LC, Ghiringhelli PD, Palermo MS. 2009. A DNA vaccine encoding the enterohemorragic *Escherichia coli* Shiga-like toxin 2 A2 and B subunits confers protective immunity to Shiga toxin challenge in the murine model. Clin. Vaccine Immunol 16:712-718.

Cai K, Gao X, Li T, Wang Q, Hou X, Tu W, Xiao L, Tian M, Liu Y, Wang H. 2011. Enhanced immunogenicity of a novel Stx2Am-Stx1 B fusion protein in a mice model of enterohemorrhagic *Escherichia coli* 0157:H7 infection. Vaccine 29:946-952.

Chen J, Lin L, Li N, She F. 2012. Enhancement of *Helicobacter pylori* outer inflammatory protein DNA vaccine efficacy by co-delivery of interleukin-2 and B subunit heat-labile toxin gene encoded plasmids. Microbiol Immunol 56:85-92.

Cheng Y, Feng Y, Luo P, Gu J, Yu S, Zhang WJ, Liu YQ, Wang QX, Zou QM, Mao XH. 2009. Fusion expression and immunogenicity of EHEC EspA-Stx2AI protein: implications for the vaccine development. J Microbial 47:498-505.

Fan HY, Wang L, Luo J, Long BG. 2012. Protection against *Escherichia coli* 0157:H7 challenge by immunization of mice with purified Tir proteins. Mol Bioi Rep 39:989-997.

Fujii J, Naito M, Yutsudo T, Matsumoto S, Heatherly DP, Yamada T, Kobayashi H, Yoshida S, Obrig T. 2012. Protection by a recombinant *Mycobacterium bovis* Bacillus Calmette-Guerin vaccine expressing Shiga toxin 2 B subunit against Shiga toxin producing *Escherichia coli* in mice. Clin Vaccine Immunol 19:1932-1937.

Gall, D. "The adjuvant activity of aliphatic nitrogenous bases", (1966) Immunology 11:369-386.

Gao X, Cai K, LiT, Wang Q, Hou X, Tian R, Liu H, Tu W, Xiao L, Fang L, Luo S, Liu Y, Wang H. 2011. Novel fusion protein protects against adherence and toxicity of enterohemorrhagic *Escherichia coli* 0157:H7 in mice. Vaccine 29:6656-6663.

Gao X, Cai K, Shi J, Liu H, Hou X, Tu W, Xiao L, Wang Q, Wang H. 2009. Immunogenicity of a novel Stx2B-Stx1 B fusion protein in a mice model of Enterohemorrhagic *Escherichia coli* 0157:H7 infection. Vaccine 27:2070-2076.

(Continued)

*Primary Examiner* — Patricia Duffy

(74) *Attorney, Agent, or Firm* — Norton Rose Fulbright US LLP

(57) ABSTRACT

Certain embodiments are directed to compositions comprising EHEC-specific antigens. In certain aspects EHEC O157:H7-specific antigen(s) are used as components of immunogenic compositions and vaccines.

7 Claims, 5 Drawing Sheets

Specification includes a Sequence Listing.

(56) References Cited

OTHER PUBLICATIONS

Garcia-Angulo VA, Kalita A, Torres AG. 2013. Advances in the development of enterohemorrhagic *Escherichia coli* vaccines using murine models of infection. Vaccine 31 :3229-3235.
Gu J, Liu Y, Yu S, Wang H, Wang Q, Vi Y, Zhu F, Yu XJ, Zou Q, Mao X. 2009. Enterohemorrhagic *Escherichia coli* trivalent recombinant vaccine containing EspA, intimin and Stx2 induces strong humoral immune response and confers protection in mice. Microbes Infect 11 :835-841.
Gu J, Ning Y, Wang H, Xiao 0, Tang B, Luo P, Cheng Y, Jiang M, LiN, Zou Q, Mao X. 2011. Vaccination of attenuated EIS-producing *Salmonella* induces protective immunity against enterohemorrhagic *Escherichia coli* in mice. Vaccine 29:7395-7403.
Ishikawa S, Kawahara K, Kagami Y, Isshiki Y, Kaneko A, Matsui H, Okada N, Danbara H. 2003. Protection against Shiga toxin 1 challenge by immunization of mice with purified mutant Shiga toxin 1. Infect Immun 71 :3235-3239.
Kalita et al. "Exploiting the power of OMICS approaches to produce *E. coli* O157 vaccines" *Gut Microbes* 5(6):770-74, 2014.
Liang Y, Wu X, Zhang J, Xiao L, Yang Y, Bai X, Yu Q, LiZ, Bi L, LiN, Wu X. 2012. Immunogenicity and therapeutic effects of Ag85A/B chimeric DNA vaccine in mice infected with *Mycobacterium tuberculosis*. FEMS Immunol Med Microbiol 66:419-426.
Marcato P, Mulvey G, Read RJ, Vander Helm K, Nation PN, Armstrong GO. 2001. Immunoprophylactic potential of cloned Shiga toxin 2 B subunit. J Infect Dis 183:435-443.
Matthews L, Reeve R, Gaily DL, Low JC, Woolhouse ME, McAteer SP, Locking ME, Chase-Topping ME, Haydon DT, Allison LJ, Hanson MF, Gunn GJ, Reid SW. 2013. Predicting the public health benefit of vaccinating cattle against *Escherichia coli* 0157. Proc Natl Acad Sci USA 110:16265-16270.
Matthews L, Reeve R, Woolhouse ME, Chase-Topping M, Mellor DJ, Pearce MC, Allison LJ, Gunn GJ, Low JC, Reid SW. 2009. Exploiting strain diversity to expose transmission heterogeneities and predict the impact of targeting supershedding. Epidemics 1:221-229.
Mejias MP, Ghersi G, Craig PO, Panek CA, Bentancor LV, Baschkier A, Goldbaum FA, Zylberman V, Palermo MS. 2013. Immunization with a chimera consisting of the B subunit of Shiga toxin type 2 and *Brucella* lumazine synthase confers total protection Shiga toxins in mice. J Immunol 191:2403-2411.
Neupane M, Abu-Aii GS, Mitra A, Lacher OW, Manning SO, Riordan JT. 2011. Shiga toxin 2 overexpression in *Escherichia coli* 0157:II7 strains associated with severe human disease. Microb Pathog 51:466-470.
Rojas RL, Gomes PA, Bentancor LV, Sbrogio-Aimeida ME, Costa SO, Massis LM, Ferreira RC, Palermo MS, Ferreira LC. 2010. *Salmonella enterica* serovar Typhimurium vaccine strains expressing a nontoxic Shiga-like toxin 2 derivative induce partial protective immunity to the toxin expressed by enterohemorrhagic *Escherichia coli*. Clin Vaccine Immunol 17:529-536.
Schijns et al., "Immunological concepts of vaccine adjuvant activity", Curr. Opi. Immunol. (2000) 12:456-63.
Snedeker KG, Campbell M, Sargeant JM. 2012. A systematic review of vaccinations to reduce the shedding of *Escherichia coli* 0157 in the faeces of domestic ruminants. Zoonoses Public Health 59:126-138.
Varela NP, Dick P, Wilson J. 2013. Assessing the existing information on the efficacy of bovine vaccination against *Escherichia coli* 0157:H7—a systematic review and metaanalysis. Zoonoses Public Health 60:253-268.
Walle KV, Vanrompay D, Cox E. 2012. Bovine innate and adaptive immune responses against *Escherichia coli* 0157:H7 and vaccination strategies to reduce faecal shedding in ruminants. Vet Immunol Immunopathol 152:109-120.
Wan CS, Zhou Y, Yu Y, Peng LJ, Zhao W, Zheng XL. 2011. B-cell epitope KT-12 of enterohemorrhagic *Escherichia coli* 0157:H7: a novel peptide vaccine candidate. Microbiol Immunol 55:247-253.
Zhang XH, He KW, Zhang SX, Lu WC, Zhao PO, Luan XT, Ye Q, Wen LB, Li 8, Guo RL, Wang XM, Lv LX, Zhou JM, Yu ZV, Mao AH. 2011. Subcutaneous and intranasal immunization with Stx2B-Tir-Stx1 B-Zot reduces colonization and shedding of *Escherichia coli* 0157:H7 in mice. Vaccine 29:3923-3939.
Zhang XH, He KW, Zhao PO, Ye Q, Luan XT, Yu ZV, Wen LB, Ni YX, Li B, Wang XM, Guo RL, Zhou JM, Mao AH. 2012. Intranasal immunisation with Stx2B-Tir-Stx1 B-Zot protein leads to decreased shedding in goats after challenge with *Escherichia coli* 0157:H7. Vet Rec 170:178.

* cited by examiner

A.

B.

| S No. (Gene Name) | Length (aa) | Th2 MED Score | # Alleles Covered |
|---|---|---|---|
| P24 (*lomP*) | 199 | 29.57277 | 12 |
| P10 (*lomW*) | 244 | 25.41398 | 13 |
| P56 (*escC*) | 512 | 24.42143 | 14 |
| P41 (*escJ*) | 244 | 23.75636 | 14 |
| P34 (Z3310) | 199 | 22.96545 | 9 |
| P58 (Z5220) | 360 | 21.93267 | 12 |
| P31 (*lomU*) | 199 | 21.62199 | 8 |
| P59 (Z5221) | 356 | 21.52184 | 12 |
| P12 (*fimA*) | 186 | 20.18483 | 9 |
| P53 (Z5110) | 934 | 18.21436 | 14 |
| P60 (*fimD*) | 844 | 17.33995 | 13 |
| P46 (Z4965) | 176 | 16.39762 | 5 |
| P42 (Z4197) | 567 | 16.13882 | 13 |
| P45 (*chuA*) | 660 | 15.92071 | 14 |
| P14 (Z1543) | 539 | 15.53107 | 13 |
| P44 (Z4386) | 713 | 15.27716 | 14 |
| P15 (Z1617) | 696 | 13.86134 | 15 |

COMPOSITIONS AND METHODS FOR ENTEROHEMORRHAGIC *ESCHERICHIA COLI* (EHEC) VACCINATION

PRIORITY

The present application is a continuation-in-part from U.S. application Ser. No. 14/638,956 filed Mar. 4, 2015, which claims priority to U.S. Application No. 61/948,001 filed Mar. 4, 2014. Each of which is incorporated herein by reference in its entirety.

STATEMENT REGARDING FEDERALLY FUNDED RESEARCH

This invention was made with government support under R21AI09956001 awarded by the National Institutes of Health. The government has certain rights in the invention.

BACKGROUND

Enterohemorrhagic *Escherichia coli* (EHEC) O157:H7 strains are major human food-borne pathogens, responsible for bloody diarrhea and hemolytic uremic syndrome (HUS). So far, there is no vaccine for humans against EHEC infections.

Enterohemorrhagic *Escherichia coli* (EHEC) strains are zoonotic extracellular pathogens, members of the Shiga-toxin producing *E. coli* (EHEC) pathogroup. EHEC causes sporadic outbreaks of diarrhea and hemorrhagic colitis, particularly in developed countries (reviewed in Nataro and Kaper, 1998, *Clin Microbial Rev* 11:142-201; Farfan and Torres, 2012, *Infect lmmun* 80:903-13; Nguyen and Sperandio, 2012, *Front Cell Infect Microbial* 2:90). In the United States, EHEC causes approximately 0.9 cases per 100,000 inhabitants, with a significant number of hospitalizations and death, particularly among children and the elderly (reviewed in Garcia-Angulo et al., 2013, *Vaccine* 31:3229-35; Marks et al., 2013, *J Food Prot* 76:945-52). *E. coli O*157:H7 comprises the serotype most commonly associated with outbreaks (Karmali et al., 2010, *Vet Microbiol* 140:360-70) and the expression of Shiga toxin (Stx), in addition to be linked to hemorrhagic colitis, it is associated with the progression to the hemolytic uremic syndrome (HUS), which cause renal failure and high fatality rate [reviewed in (Pacheco and Sperandio, 2012, *Front Cell Infect Microbial* 2:81)]. In addition, EHEC O157:H7 uses a type 3 secretion system (T3SS) to translocate effector proteins into the eukaryotic cell, causing changes in the host cytoskeleton, ultimately leading to improved bacterial adherence and colonization and, in some cases, host cell death (Wong et al., 2011, *Mol Microbiol* 80:1420-38). The EHEC T3SS is comprised of a basal ATP-dependent secretion apparatus, with an EscC polymer ring spanning bacterial outer membrane and a needle like structure formed by polymers of the EscF protein and an extension structure comprised of polymerized EspA. Finally, the EspD and EspB proteins form a translocon structure in the host membrane (Sekiya et al., 2001, *Proc Natl Acad Sci USA* 98:11638-43; Spreter et al., 2009, *Nat Struct Mol Biol* 16:468-76; Tree et al., 2009, *Trends Microbial* 17:361-70).

Generally asymptomatic, ruminants are the principal EHEC reservoir. Contaminated meat or fresh produce resulting from animal shedding constitutes an important route for human infection (Walle et al., 2012, *Vet Immunol Immunopathol* 152:109-20). Current prevention efforts are centered in the elimination of animal colonization, whether by vaccination or by improving sanitary and breeding practices (Walle et al., 2012, *Vet Immunol Immunopathol* 152:109-20; Varela et al., 2013, *Zoonoses Public Health* 60:253-68). Once the human infection is acquired, supportive care is provided, since antibiotic treatment could induce Shiga toxin expression. To date, two vaccines able to reduce EHEC colonization in cattle are commercially available (Varela et al., 2013, *Zoonoses Public Health* 60:253-68; Snedeker et al., 2012, *Zoonoses Public Health* 59:126-38). Nevertheless, development of other subunit-based vaccines has been focused in the T3SS and its associated proteins, as well as Stx (Garcia-Angulo et al., 2013, *Vaccine* 31:3229-35; Walle et al., 2012, *Vet Immunol Immunopathol* 152:109-20). For example, inactivated Stx-derivatives are able to induce Stx-neutralizing antibodies in mice (Ishikawa et al., 2003, *Infect Immun* 71:3235-39; Marcato et al., 2001, *J Infect Dis* 183:435-43) and hybrid A-B subunit-derived Stx toxins also induce antibody production and increase survival against toxemia and EHEC challenge in vivo (Cai et al., 2011, *Vaccine* 29:946-52; Bentancor et al., 2009, *Clin Vaccine Immunol* 16:712-18; Rojas et al., 2010, *Clin Vaccine Immunol* 17:529-36). Fusion proteins comprising of Stx-derived peptides and T3SS-related proteins are promising vaccine candidates. St2B-Tir-Stx1 B-Zot, Stx2B-Stx1 B-lnt281, EspA-Stx2A 1, EspA-IntiminC300-Stx2B and Stx2B-BLS fusions have been demonstrated to reduce EHEC colonization in animal models, such as mice and goats (Cheng et al., 2009, *J Microbial* 47:498-505; Gu et al., 2009, *Microbes Infect* 11:835-41; Gu et al., 2011, *Vaccine* 29:7395-03; Zhang et al., 2011, *Vaccine* 29:3923-39; Zhang et al., 2012, *Vet Rec* 170:178; Gao et al., 2009, *Vaccine* 27:2070-76; Gao et al., 2011, *Vaccine* 29:6656-63; Mejias et al., 2013, *J Immunol* 191:2403-11). Overall, cumulative information indicates that mucosal delivery routes seem to be an effective way to induce immune responses to block the adhesion of EHEC in the intestine, mainly through expression of secretory lgA (slgA) (Garcia-Angulo et al., 2013, *Vaccine* 31:3229-35).

In addition to the worldwide outbreaks caused by EHEC O157:H7, this organism has come recently under renewed scientific investigation as a result of the emergence of a subpopulation of strains that have acquired critical virulence factors that contribute to more severe and lethal disease in humans (Abu-Aii et al., 2010, *PLoS One* 5:e10167; Neupane et al., 2011, *Microb Pathog* 51:466-70). Further, the discovery of cattle reservoirs shedding high levels of EHEC O157:H7, which has been associated with the transmission between animals and across the human-animal interface (Arthur et al., 2013, *Appl Environ Microbial* 79:4294-4303; Matthews et al., 2009, *Epidemics* 1:221-29), strongly supports the idea that adoption of vaccination for livestock and/or susceptible individuals will have significant public health benefits, preventing substantial numbers of human EHEC O157 cases (Matthews et al., 2013, *Proc Natl Acad Sci USA* 110:16265-70). Therefore, further discovery for EHEC-specific antigens needs to be done to improve existing or to develop novel vaccines.

SUMMARY

Because the EHEC-associated disease is complex and many molecular and cellular processes affected during infection are not fully understood, it is plausible to propose that some EHEC-encoded virulence-associated proteins could have important, yet unveiled role in the immune/protective process. Therefore, in order to bypass the bias towards assaying a limited number of known virulence factors as components of a vaccine against O157:H7, the inventor performed a genome-wide in silico search for proteins most likely to be effective as immunogenic/protective antigens. By comparative genomics, EHEC-specific antigens were identified with high probability to be exposed to the host during infection. Using an immunoinformatics approach, the candidates were further grouped into high, medium, and low priority groups based on their putative antigenicity and screened as vaccine candidates in a murine model of gastrointestinal infection. Three candidates from each group were selected and evaluated as DNA vaccines for their capacity to induce an EHEC immune response and to reduce bacterial colonization in the murine intestine.

Certain embodiments are directed to compositions comprising EHEC-specific antigens. In certain aspects EHEC O157:H7-specific antigen(s) are used as components of immunogenic compositions and vaccines. Vaccines described herein are able to protect against pathogenic *E. coli* infections without affecting commensal flora. EHEC O157 specific antigens were identified as having a high probability of being exposed to the host during infection. Subsequently, an immunoinformatics approach was used to group EHEC O157 specific antigens into priority groups (high, medium and low) based on their antigenicity. Screening of these identified antigens in a murine model of gastrointestinal infection demonstrated EHEC-specific immune responses and a reduction in EHEC colonization of the murine intestine particularly associated with the high priority group. These high priority antigens displayed protective properties or vaccination properties as tested in the murine model of infection.

In certain aspects the antigens described herein can be formulated in an immunogenic or vaccine composition. The composition may include an adjuvant and/or an anti-microbial agent. Certain embodiments are directed to a composition that stimulates an immune response against EHEC antigens. In certain aspects the immune response can be a therapeutic immune response treating an infection in a mammal or a protective immune response preventing EHEC related disease in a mammal. In certain aspects the compositions provide a vaccine effective to reduce, prevent and/or eliminate EHEC colonization of a ruminant or other mammal. In certain aspects the induced immune response reduces shedding of EHEC into the environment from a treated mammal. In certain aspects the mammal is an infected mammal, such as a bovine, an ovine, a suinae, or homo sapien (human). In a further aspect the administration of the antigen compositions can reduce EHEC contamination of the environment, food products, and/or water.

Certain embodiments are directed to a vaccine composition comprising an enterohemorragic *E. coli* (EHEC) specific antigen(s) and an immunological adjuvant. In certain embodiments, the EHEC is EHEC O157:H7, EHEC EDL933, EHEC Sakai, and/or EHEC O157. In additional embodiments, the immunological adjuvant comprises an oil-in-water emulsion, such as a mineral oil and dimethyldioctadecylammonium bromide. In yet additional embodiments, an adjuvant is present at a concentration of about 20% to about 40% (v/v), such as at a concentration of 30% (v/v).

Further embodiments are directed to methods for eliciting an immunological response in a mammal against an enterohemorragic *E. coli* (EHEC) antigen. In certain aspects the method comprises administering to a mammal a therapeutically effective amount of a composition comprising a nucleic acid encoding an EHEC antigen that is expressed when introduced to a mammal. In additional embodiments, the mammal is a human or a ruminant, such as a bovine. In yet further embodiments, the composition further comprises an adjuvant.

Still further embodiments are directed to methods for reducing colonization of enterohemorragic *E. coli* (EHEC) in a mammal comprising administering to the mammal a therapeutically effective amount of a composition comprising an EHEC antigen as described herein.

Particular embodiments are directed to methods for reducing Enterohemorrhagic *Escherichia coli* (EHEC) cecum colonization in a subject comprising providing to a subject a therapeutic amount of a polypeptide having an amino acid sequence of LomW (SEQ ID NO:22), EscJ (SEQ ID NO:23), EscC (SEQ ID NO:3), or a combination thereof. The polypeptide can be provided by administering one or more expression vector that encodes one or more polypeptide. In certain aspects the subject is a ruminant. In a further aspect the subject is bovine or human. In certain aspects the subject is provided (a) a polypeptide having an amino acid sequence of SEQ ID NO:22, SEQ ID NO:23, SEQ ID NO:3, or a combination thereof and (b) a polypeptide having the amino acid sequence of (i) SEQ ID NO:22, and SEQ ID NO:23 or SEQ ID NO:3, or (ii) SEQ ID NO:23, and SEQ ID NO:22, or SEQ ID NO:3, or (iii) SEQ ID NO:22, SEQ ID NO:23, and SEQ ID NO:3. In certain aspects an expression vector is administered intranasally. The polypeptide can be provided as a priming dose followed by 1, 2, 3, 4, 5, 6, or more boosting doses.

Certain embodiments are directed to an immunogenic composition comprising a nucleic acid encoding a polypeptide or a polypeptide having an amino acid sequence of SEQ ID NO:22 or SEQ ID NO:23 in a therapeutic formulation. In certain aspects the composition comprises a nucleic acid encoding a polypeptide or a polypeptide having an amino acid sequence of SEQ ID NO:22 and a polypeptide having an amino acid sequence of SEQ ID NO:23. In ca further aspect the composition further comprises a polypeptide having an amino acid sequence of SEQ ID NO:3.

Other embodiments of the invention are directed to methods for stimulating an immune response to an Enterohemorrhagic *Escherichia coli* (EHEC) in a subject comprising providing an immunogenic composition having a nucleic acid encoding a polypeptide or a polypeptide having an amino acid sequence of SEQ ID NO:22, SEQ ID NO:23, SEQ ID NO:3, or combinations thereof in a therapeutic formulation. In certain aspects the polypeptides are encoded by one or more expression vector. In a further aspect the subject is a bovine or a human.

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen, e.g., three-dimensional conformation or modification (e.g., phosphorylation), giving rise to a biological response is referred to herein as an "antigenic determinant" or "epitope." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MEW, by T-cell receptors. An antigenic determinant need not be a contiguous sequence or segment of protein and may include various sequences that are not immediately adjacent to one another. In certain embodiments, binding moieties other than antibodies can be engineered to specifically bind to an antigen, e.g., aptamers, avimers, and the like.

The term "antibody" or "immunoglobulin" is used to include intact antibodies and binding fragments/segments thereof. Typically, fragments compete with the intact antibody from which they were derived for specific binding to an antigen. Fragments include separate heavy chains, light chains, Fab, Fab' F(ab')2, Fabc, and Fv. Fragments/segments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibodies. A bispecific or bifunctional antibody is an artificial hybrid antibody having two different heavy/light chain pairs and two different binding sites. Bispecific antibodies can be produced by a variety of methods including fusion of hybridomas or linking of Fab' fragments (See, e.g., Songsivilai and Lachmann, 1990, *Clin Exp Immunol* 79:315-21; Kostelny et al., 1992, *J. Immunol.* 148:1547-53).

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

As used herein, a "recombinant" EHEC secreted protein refers to the full-length polypeptide sequence, fragments of the reference sequence or substitutions, deletions and/or additions to the reference sequence, so long as the proteins retain effectiveness in the animal models described herein. Generally, variants of an antigen will display at least about 90% sequence identity, preferably at least about 95% to 99% sequence identity to the full-length reference sequence or an immunogenic portion thereof. Percent sequence identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353-58, National biomedical Research Foundation, Washington, D.C., which adapts the local homology algorithm of Smith and Waterman (1981) *Advances in Appl. Math.* 2:482-89 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

As used herein, "colonization" refers to the presence of EHEC in the intestinal tract of a mammal.

As used herein, "shedding" refers to the presence of EHEC in feces.

As used herein, "therapeutic amount", "effective amount" and "amount effective to" refer to an amount of vaccine effective to elicit an immune response against a secreted antigen, thereby reducing or preventing EHEC disease, and/or EHEC colonization of a mammal, e.g., a ruminant or human; and/or reducing the shedding of EHEC; and/or reducing the number of EHEC shed by a mammal; and/or, reducing the time period of EHEC shedding by a mammal.

As used herein, "immunization" or "immunize" refers to administration of an immunogenic composition in an amount effective to stimulate the immune system of an animal or mammal to which the composition is administered and elicit an immunological response against one or more antigens present in the composition.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display either a therapeutic or protective immunological response such that EHEC disease is lessened and/or prevented; resistance of the intestine to colonization with EHEC is imparted; shedding of EHEC is reduced; the number of EHEC shed by a mammal is reduced; and/or the time period of EHEC shedding by a mammal is reduced.

The terms "immunogenic" protein or polypeptide refer to an amino acid sequence that elicits an immunological response as described above. An "immunogenic" protein or polypeptide, as used herein, includes the full-length sequence of the particular EHEC protein in question, analogs thereof, aggregates, or immunogenic fragments thereof. By "immunogenic fragment" is meant a fragment of a secreted EHEC protein that includes one or more epitopes and thus elicits the immunological response described above. Such fragments can be identified using any number of epitope mapping techniques well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984 *Proc. Natl. Acad. Sci. USA* 81:3998-4002; Geysen et al., 1986 *Molec. Immunol.* 23:709-15, all incorporated herein by reference in their entireties. Similarly, conformational epitopes are identified by determining spatial conformation of amino acids (e.g., using x-ray crystallography and 2-dimensional nuclear magnetic resonance). Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., 1981, *Proc. Natl. Acad. Sci USA* 78:3824-28 for determining antigenicity profiles, and the Kyte-Doolittle technique, Kyte et al., 1982 *J. Mol. Biol.* 157:105-32 for hydropathy plots.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

The term "treatment" as used herein refers to either (i) the prevention of infection or reinfection (prophylaxis), or (ii) the reduction or elimination of symptoms of the disease of interest (therapy).

By "mammalian subject" is meant any member of the class Mammalia, including humans and other mammary gland possessing animals, such as ruminants, including, but not limited to, bovine, porcine, and ovine (sheep and goats) species.

Moieties of the invention, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation."

The term "providing" is used according to its ordinary meaning "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes.

The phrase "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figures 1A, 1B:
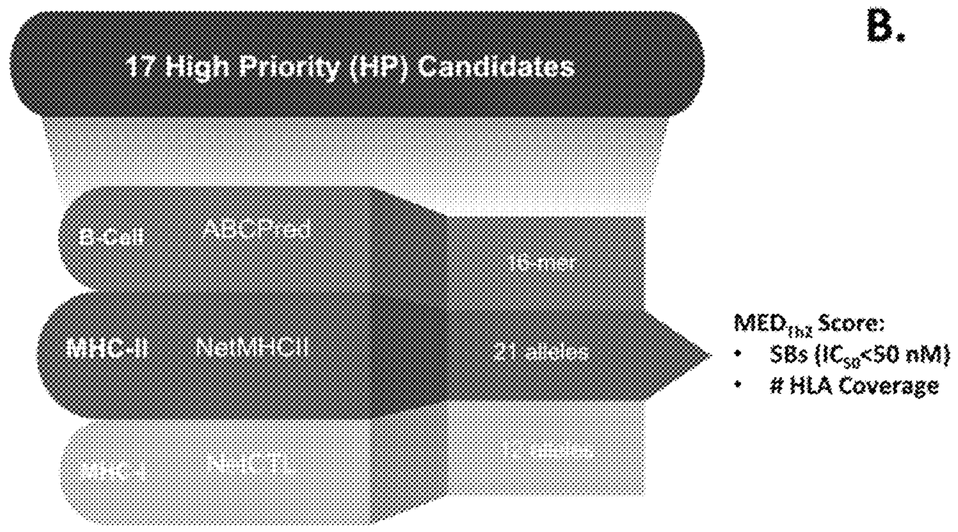
FIGS. 1A-1B. Classification of Identified Candidates. (A) Schematic representing prediction strategy for candidate selection of HP candidates. (B) Table showing individual candidates along with their compiled $MED_{Th2}$ score and allele coverage across 17 high-priority candidates. The input to the equation was MHC-II prediction results (NetMHCII) only. Hence, it is expected to provide us with Th2-oriented inference.

Certain embodiments of the invention identify vaccine candidates by screening the density of immunogenic epitopes within highly ranked proteins. By performing a mature epitope density (MED) prediction, candidates were clustered based on similarities in putative immunogenic Th2 epitopes ($MED_{Th2}$). This method allowed the identification of two new candidates, lomW (locus AE005298_8)(SEQ ID NO:22), a gene encoding a putative outer-membrane protein belonging to the Lom precursor of a bacteriophage Bp-933W, and escJ gene (locus AE005514_9)(SEQ ID NO:23), encoding a putative lipoprotein associated with the T3SS. These candidates were cloned in pVAX1 vector and administered intranasally to BALB/c mice. Upon vaccination, it was observed that the largest increase in sIgA levels from lomW in comparison to escC and escJ. While no significant difference was detected in total IgG levels, a significant reduction in bacterial adhesion to intestinal epithelial cells in vitro and reduced colonization in a murine model of EHEC O157:H7 infection was seen.

Most EHEC subunit vaccine candidates tested to date are comprised of known virulence factors, such as Stx and the T3SS-related proteins. These virulence factors are well characterized and known to be essential for the onset of EHEC colonization and/or host damage. Further, it is well documented that the main protection mechanism for these vaccine candidates is the induction of neutralizing antibodies (Garcia-Angulo et al., 2013 *Vaccine* 31:3229-35). However, the DNA sequences encoded in the genome of EHEC strains may contain unveiled genes encoding antigenic proteins that have not yet been investigated as vaccine candidates. Computational vaccinology tools have been proposed as a potentially powerful aid in vaccine development, particularly for new or emerging pathogens from which critical antigenic determinants and/or virulence factors knowledge is limited (De Groot et al., 2012 *Hum Vaccin lmmunother* 8:987-1000). The methods described herein combines comparative genomics and immunoinformatics analysis of available EHEC genomes in the search for vaccine candidates. This approach represents an unbiased screening method, as it seeks in the encoded sequences irrespective of their putative or experimental function, which allows the discovery of potential candidates overlooked by other EHEC vaccine studies. Use of this method led to an initial list of 65 vaccine candidates, three of which were proven to be able to induce immune responses, and one of them also reduced EHEC colonization when delivered as a DNA vaccine.

Enterohemorrhagic *E. coli* (EHEC) O157:H7 strains are major human food-borne pathogens, responsible for bloody diarrhea and hemolytic uremic syndrome (HUS). So far, there is no vaccine for humans against EHEC infections. Comparative genomics analysis was performed to identify EHEC-specific antigens useful as potential vaccines. The genes are present in both EHEC EDL933 and Sakai strains but absent in non-pathogenic *E. coli* K-12 and HS strains. The EHEC genes were subjected to an in silico analysis to identify secreted or surface-expressed proteins. The inventor identified 65 gene-encoding protein candidates that were subjected to immunoinformatics analysis. The candidates were categorized as high priority (HP), medium priority (MP), and low priority (LP). Three members of each group were selected and cloned into pVAX-1. Candidates were pooled accordingly to their priority group and tested for immunogenicity against EHEC O157:H7 using a murine model of gastrointestinal infection. The high priority (HP) pool, containing genes encoding for a Lom-like protein (pVAX-31)(SEQ ID NO:1), a putative pilin subunit (pVAX-12)(SEQ ID NO:2), and a fragment of the type III secretion structural protein EscC (pVAX-56.2)(SEQ ID NO:3), was able to induce the production of EHEC specific lgG and sIgA in sera and feces. HP-immunized mice displayed elevated levels of Th2 cytokines and diminished cecum colonization after wt challenge. Individually tested HP-vaccine candidates showed that pVAX-12 and pVAX-56.2 significantly induced Th2 cytokines and production of fecal EHEC sIgA, with pVAX-56.2 reducing EHEC cecum colonization. The bioinformatics approach described herein is able to identify vaccine candidates useful to prevent EHEC O157:H7 infections.

As intestinal mucosal surfaces are composed of exposed tissue in permanent contact with harmless environmental bacteria, which likely participate in maintenance of a homeostasis state (Cieza et al., 2012 *Expert Rev Anti Infect Ther* 10:391-400), immune responses are relatively difficult to induce by vaccine candidates delivered in the gastrointestinal mucosa. The HP antigens described herein were able to induce EHEC humoral responses both in serum and in intestinal mucosa. Although some candidates assayed in mice have been shown to be protective by inducing exclusively serum responses (Cheng et al., 2009 *J Microbial* 47:498-505; Babiuk et al., 2008 *Microb Pathog* 45:7-11), most involved the production of sIgA (Cai et al., 2011 *Vaccine* 29:946-52; Fan et al., 2012 *Mol Biol Rep* 39:989-97; Fujii et al., 2012 *Clin Vaccine Immunol* 19:1932-37; Wan et al., 2011 *Microbiol Immunol* 55:247-53; Amani et al., 2011 *Plant Sci* 180:620-27). In this case, the induction of sIgA by the HP pool correlated with a reduction in colonization, while the MP pool was also able to increase serum IgG levels but failed to reduce EHEC colonization after challenge. Assays performed with the three representative HP candidates individually also seem to support the role of intestinal mucosa humoral response in protection, as pVAX-12 failed to protect against EHEC colonization, despite inducing a strong serum humoral response. On the other hand, pVAX-56.2, the candidate inducing the highest sIgA titers in feces, was able to cause a reduction of bacterial load in cecum. In certain aspects the combined immune response induced by the three representative HP antigens achieves colonization reduction levels.

Certain embodiments will employ conventional techniques of molecular biology, microbiology, recombinant DNA technology, and immunology, which are within the skill of the art. Such techniques are explained fully in the literature. See for example, Sambrook, Fritsch & Maniatis, *Molecular Cloning: A Laboratory Manual*, Vols. I, II and III, Second Edition (1989) and *Handbook of Experimental Immunology*, Vols. I-IV (D. M. Weir and C. C. Blackwell eds, 1986, Blackwell Scientific Publications).

I. Methods for Antigen Identification

Subunit EHEC vaccine research has been mainly focused on known virulence factors. The inventor sought to screen the genome of EHEC strains EDL933 and Sakai to identify sequences with a high probability to encode protective antigens, independently of their previous assigned function. Mucosal immune responses are relatively difficult to induce by vaccine candidates due to the fact that mucosal surfaces are often in contact with non-pathogenic *E. coli*, which enhance the homeostatic state [reviewed in Cieza et al., 2012 *Expert Rev Anti Infect Ther* 10:391-400]. Thus, a first criterion was to identify common EHEC antigens absent in non-pathogenic *E. coli* strains. For this, the set of common proteins between EDL933 and Sakai O157:H7 EHEC strains were determined by a reciprocal BLAST analysis as described below. Next, those DNA sequences encoding proteins present in the non-pathogenic *E. coli* K-12 MG1655 and commensal HS strains genomes were eliminated from the pool. This analysis rendered 897 protein sequences. It is proposed that the probabilities to provide protection increase for those antigens detected during natural infection, meaning that bacterial-exposed proteins comprise better vaccine candidates (Barat et al., 2012 *PLoS Pathog* 8:e1002966). In order to predict their subcellular localization, the 897 proteins selected in the previous analysis were fed to the P-SORTb software (available on the worldwide web at psort.org/psortb/). A total of 65 proteins putatively associated with the outer membrane and/or secreted were selected as vaccine candidates (Table 1).

TABLE 1

EHEC O157-specific secreted and outer membrane associated proteins identified by P-SORT analysis.

| # | GI number | Annotation |
|---|---|---|
| 1 | 12512859 | putative fimbrial protein |
| 2 | 12512975 | hypothetical protein Z0266 |
| 3 | 12513130 | putative beta-barrel outer membrane protein |
| 4 | 12513211 | putative structural protein (partial) |
| 5 | 12513363 | putative outer membrane export protein |
| 6 | 12513364 | hypothetical protein Z0609 |
| 7 | 12513368 | putative RTX family exoprotein |
| 8 | 12513376 | hypothetical protein Z0639 |
| 9 | 12513752 | putative outer membrane protein of prophage CP-933K |
| 10 | 12514345 | putative outer membrane protein Lom precursor of protein bacteriophage BP-933W |
| 11 | 12514376 | hypothetical protein Z1516 |
| 12 | 12514403 | putative pilin subunit |
| 13 | 12514410 | putative member of ShiA/HecA/FhaA exoprotein family |
| 14 | 12514411 | putative outer membrane transporter of ShiA/HecA/FhaA exoprotein family |
| 15 | 12514503 | Putative receptor |
| 16 | 12514836 | putative tail component of prophage CP-933X |
| 17 | 12514898 | putative outer membrane receptor, probably tonB dependent |
| 18 | 12515102 | putative tail component of prophage CP-9330 |
| 19 | 12515159 | orf, hypothetical protein |
| 20 | 12515160 | putative ATP-binding component of a transport system and adhesion protein |
| 21 | 12515311 | putative outer membrane protein |
| 22 | 12515315 | hypothetical protein Z2323 |
| 23 | 12515551 | putative chaperone protein |
| 24 | 13259573 | putative Lom-like outer membrane protein of cryptic prophage CP-933P |

TABLE 1-continued

EHEC O157-specific secreted and outer membrane associated proteins identified by P-SORT analysis.

| # | GI number | Annotation |
|---|---|---|
| 25 | 13259574 | putative tail component of cryptic prophage CP-933P |
| 26 | 13259580 | putative tail component of cryptic prophage CP-933P |
| 27 | 12516024 | flagellar biosynthesis; flagellin, filament structural protein |
| 28 | 12516037 | putative secreted protein |
| 29 | 12516039 | putative secreted protein |
| 30 | 12516089 | unknown protein encoded within prophage CP-933U |
| 31 | 12516092 | putative outer membrane protein of prophage CP-933U |
| 32 | 12516149 | putative integrase for prophage CP-933U |
| 33 | 12516174 | putative outer membrane receptor for iron compound or colicin |
| 34 | 12516360 | putative Lorn-like outer membrane protein of prophage CP-933V |
| 35 | 12516361 | putative tail fiber protein of prophage CP-933V |
| 36 | 12516373 | putative major tail subunit encoded within prophage CP-933V |
| 37 | 169822942 | putative fimbrial usher |
| 38 | 12517052 | hypothetical protein Z3920 |
| 39 | 12517087 | hypothetical protein Z3954 |
| 40 | 12517088 | putative enzyme |
| 41 | 12517355 | putative lipoprotein of type Ill secretion apparatus |
| 42 | 12517375 | type Ill secretion apparatus protein |
| 43 | 12517526 | putative PagC-Iike membrane protein |
| 44 | 12517607 | putative iron compound receptor |
| 45 | 12518206 | outer membrane heme/hemoglobin receptor |
| 46 | 12518273 | putative fimbrial subunit |
| 47 | 12518274 | putative fimbrial protein |
| 48 | 12518278 | putative major fimbrial subunit |
| 49 | 12518349 | putative adhesin |
| 50 | 12518435 | espF |
| 51 | 12518439 | secreted protein EspB |
| 52 | 12518440 | secreted protein ExpO |
| 53 | 12518447 | intimin adherence protein |
| 54 | 12584449 | putative translocated intiminreceptor protein |
| 55 | 12518464 | escJ |
| 56 | 12518466 | escC |
| 57 | 12518483 | hypothetical protein Z5142 |
| 58 | 12518576 | putative fimbrial protein |
| 59 | 12518577 | putative fimbrial protein |
| 60 | 12518578 | putative fimbrial usher |
| 61 | 12518581 | putative major fimbrial subunit |
| 62 | 12518689 | hypothetical protein Z5335 |
| 63 | 3822134 | putative exoprotein-precursor |
| 64 | 3822145 | hypothetical protein |
| 65 | 3822162 | hypothetical toxin protein |

Nomenclature: *low priority; medium priority; *high priority candidates.
[a]We have further analyzed these final candidates using blastp and found paralogs of some of these sequences in recently sequenced non-pathogenic *E. coli* strains.

Further, the process of identifying highly antigenic vaccine candidates was accelerated by using immunoinformatics, which allowed the assignment of priorities for the testing of these vaccine candidates in the mouse model of EHEC O157:H7 infection. The proteins were prioritized on the basis of either possessing no transmembrane (TM) domains or containing one region only, having a signal peptide or whether its localization was predicted to be secreted, and whether they display a high score for adhesiveness. Proteins that satisfy more of these characteristics were ranked higher than others. The VaxiJen server (Doytchinova and Flower 2007 *BMC Bioinformatics* 8:4) predicted the protective bacterial antigens based on the overall immunogenicity score (higher was better), and also helped to rank the proteins. For B-cell epitope predictions, three parameters were calculated from results: (i) total number of epitopes per sequence, (ii) total score of all epitopes combined per sequence, and (iii) average score of an epitope. Similarly, for T-cell epitope predictions, parameters such as (i) total number of high-binding (HB) epitopes, (ii) total score of HB epitopes, (iii) percentage of HB epitopes among all epitopes predicted for a given sequence, and (iv) number of human leukocyte antigens (HLA) alleles covered by the epitopes of a given sequence, were also calculated. These parameters were also taken into account when ranking the proteins; however, a larger weight was assigned to 8-cell epitopes since EHEC is an extracellular pathogen. The final ranking of all 65 proteins was conducted using a cumulative score from both physicochemical and immunological properties. Based on the combined informatics analysis, vaccine candidates were divided in three groups: High Priority (HP, 25 candidates), Medium Priority (MP, 28 candidates) and Low Priority (LP, 12 candidates) (indicated by asterisks in Table 1).

To screen the putative protective candidates as determined by their priority score, three representative candidates were randomly selected from each group (candidates 31, 56.2 and 12 from HP group; 43, 16 and 9 from MP group; and 51, 49.1 and 49.2 from LP group) and the selected representatives were cloned into pVAX1 DNA vaccine vector (Liang et al., 2012 *FEMS Immunol Med Microbiol* 66:419-26; Chen et al., 2012 *Microbiol Immunol* 56:85-92). DNA vaccine construction comprises an approach that allows the rapid testing of several vaccine candidates instead of limiting the analysis to antigens requiring optimized expression and purification. Being EHEC an extracellular intestinal pathogen, the approach sought to induce mucosal immune responses and DNA vaccines have been shown to induce both mucosal and systemic immune responses against pathogenic bacteria antigens when delivered by the intranasal route (Sun et al., 2012 *J Dent Res* 91:941-47; Zhu et al., 2012 *Can J Microbial* 58:802-10; Zhu et al., 2012 *Can J Microbial* 58:644-52). During the cloning process in pVAX-1, large DNA sequences were divided in coding sequences with a maximum length of 1 kb. The constructs were pooled in their respective priority group and delivered intranasally in groups of 10 mice. A schedule of priming and two boosts was followed, with 60 μg of the pooled plasmids (20 μg of each individual construct) and cholera toxin (CT) as an adjuvant. Next, induction of immune responses was evaluated in vaccinated mice. First, the production of EHEC IgG was monitored in post immunized (p.i.) mice by ELISA using serum samples collected one week after the last boost. The HP- and MP-immunized mice presented higher levels of EHEC IgG compared to animals receiving buffer (TE), adjuvant (CT) alone or pVAX-1 (empty vector). Next, EHEC IgA titers in feces were determined. The HP-vaccinated mice elicited higher titers of EHEC specific sIgA compared to MP- and LP-immunized animals and control groups, though the titer declined with increased sera dilution. These results showed that although both HP and MP DNA vaccine pools induce EHEC antibody responses, only the HP group induced a higher amount of EHEC sIgA.

Two weeks after the last boost, animals were challenged with EHEC strain 86-24. Bacterial load in feces and cecum was determined from days 3-6 after infection. Results consistently showed a reduction pattern in the CFU recovered from feces in the HP vaccinated mice at days 4, 5 and 6 compared to TE buffer, CT, or pVAX-1 control groups. In addition, a reduction in the LP vaccinated group was observed at day 6, though at lower extent than that obtained in the HP group. Cecum organ platting revealed a significant reduction of over one log ($P<0.05$) in bacterial burden in HP vaccinated mice compared to the empty vector control group at day 3. No reduction was observed in the cecum of mice vaccinated with the MP- or LP-vaccinated pools. Overall, data showed that HP plasmids were more efficient in reducing EHEC colonization in the murine model.

To determine the extent of the immunogenic/protective effect of each candidate in the overall HP vaccine group, an individual plasmid vaccination experiment was performed. 60 μg of pVAX-12, pVAX-31, pVAX-56.2, or TE buffer were administered to groups of mice with the same vaccination schedule as the previous experiment. To assess the immunogenicity of individual DNA vaccines, mice sera were collected and assayed for EHEC IgG. Results showed increased EHEC IgG levels in pVAX-12. The IgG levels were also elevated with pVAX-56.2 vaccinated group compared to TE control group. The pVAX-31 plasmid failed to induce the production of EHEC IgG. In parallel, EHEC sIgA was measured in feces of all vaccinated animals to evaluate mucosal immune induction. The mice immunized with pVAX-56.2 showed increases in sIgA up to the 1:64 dilution, as compared to control animals. The pVAX-31 and, to a minor extent, pVAX-12 also increased the levels of sIgA in feces compared to TE control group. Overall, pVAX-12 produced the higher induction of serum IgG, while pVAX-56.2 was able to stimulate high titers of both serum IgG and sIgA.

Next, mice vaccinated with individual candidates were challenged with EHEC 86-24 two weeks after the last boost. Daily bacterial load in feces and cecum colonization from days 3 through 6 post infection were assessed. Results show a clear reduction of EHEC in feces in all vaccinated groups at day 6. No differences in cecum colonization are observed at day 3. However, a small reduction in EHEC CFU on the cecum from the pVAX-56.2 immunized group was detected at day 6. Overall, pVAX-56.2 consistently induced EHEC serum IgG and fecal sIgA and reduced EHEC shedding and colonization, suggesting that candidate 56.2, which encodes the C-terminal fragment of EscC was the best candidate tested.

Because the cellular immune response plays a leading role in protection and long-term immune response, the expression of cytokines in sera of HP-, MP- and LP-immunized and non-immunized mice were evaluated using a Bio-Plex assay. Eleven out of 23 inflammatory mediators were increased in HP-immunized mice compared to non-immunized mice, including the Th1 cytokines IL-1β, and TNF-α; the Th2 cytokines IL-3, IL-5, IL-6 and IL-10; the chemokines MIP-1α, MIP-1β, eotaxin, KC and MCP-1 and the growth factor GM-CSF. Pro-inflammatory cytokines such as IL-1β, TNF-α and IL-6 are increased at an early stage of immune response and play a central role in the host defense mechanism. However, increased levels of Th2 cytokines, including IL-3, IL-5, IL-6, IL-10, but not IL-4 in HP immunized mice were also detected. It is proposed that these Th2-type cytokine responses may be accounting for the generation of the humoral antibody response. Sera obtained from mice vaccinated with individual candidates pVAX-12 and pVAX-56.2 showed an increase of Th1 cytokines (IL-1β, IL-12p70, TNF-α), Th2 cytokines (IL-3, IL-5, IL-6 and IL-10), chemokines (MIP-1β, eotaxin, MCP-1, RANTES) and the GM-CSF growth factor compared to control mice.

In certain studies the prototype enterohemorrhagic *E. coli* O157:H7 strains 86-24 (Tarr et al., 1989 *J Infect Dis* 159:344-47) and EDL933 (Riley et al., 1983 *N Engl J Med* 308:681-85) were grown in Luria Bertani (LB) broth at 37° C. Strains bearing pVAX1-derivatives were grown in medium supplemented with kanamycin (Sigma, 25 μg/ml) as requirement for recombinant plasmid selection.

A comparative bioinformatic analysis was developed to obtain groups of orthologous proteins of *E. coli* O157:H7 strains that excluded orthologous proteins from other non-pathogenic (named external) strains. To achieve this, two *E. coli* O157:H7 strains (EDL933 and Sakai) were included and two external strains: *E. coli* HS and *E. coli* K-12 strain MG1655. The most probable set of orthologous proteins shared by the two *E. coli* O157:H7 strains were identified using a reciprocal best-hit criterion as follows. All the predicted proteins of one genome were searched against the predicted proteins of the other genome and vice versa using BLAST-P with a cutoff e-value of $10^{-12}$. To be included in an ortholog group, the alignment region between the subject protein and the query protein had to be at least of 80%, and there had to be at least 40% similarity for both query and target sizes. Next, the orthologs groups that contained a protein of any of the two external strains were excluded. This resulted in a set of 897 groups of orthologous proteins shared only by the *E. coli* O157:H7 strains. The ortholog sequences corresponding to the EDL933 strain were analyzed by the P-SORT software (available on the worldwide web at psort.org/psortb/) in order to predict their subcellular localization. Sixty five proteins that were putatively secreted or outer membrane-associated were selected as candidates. These proteins were extensively analyzed for critical features found in vaccine candidates such as physicochemical properties, adhesiveness and antigenicity, and subsequently predicted for immunodominant epitopes. At least two different software programs were used for each property as described below. In most cases, the underlying principle of these programs for the same categorical property is different to ensure wide coverage yet maintaining stringency by creating a consensus of predicted results (Table 2).

initial analysis with PsortB (Yu et al., 2010 *Bioinformatics* 26:1608-15), the signal or localization peptides were also predicted using SignaiP (Petersen et al., 2011 *Nat Methods* 8:785-86) and NetChop (Kesmir et al., 2002 *Protein Eng* 15:287-96). The presence of lipoprotein signal peptide was determined using the method described by Juncker et al (2003 *Protein Sci* 12:1652-62), which predicts both SpI and SpII signal peptidases. Lipo program (Berven et al., 2006 *Arch Microbiol* 184:362-77) recognizes the lipo-box in protein sequences and was also used. SPAAN (Sachdeva et al., 2005 *Bioinformatics* 21:483-91) predicts the probability of a protein being an adhesin, which often comprise important factors in bacterial virulence. VaxiJen (Doytchinova and Flower, 2007 *BMC Bioinformatics* 8:4), an alignment-free approach for antigen prediction was used to score the overall antigenicity of the protein. VaxiJen model used was “bacteria” with threshold set to 0.5. 8-cell linear epitopes were predicted using ABCPred (Saha and Raghava, 2006 *Proteins* 65:40-48) while NetCTL (Larsen et al., 2007 *BMC Bioinformatics* 8:424) and NetMHC-II (Nielsen and Lund, 2009 *BMC Bioinformatics* 10:296) programs were used to predict MHC class I and class II binding peptides, respectively. The ABCPred provided an accuracy of 65.93% and equal sensitivity and specificity using window length of 16-mer peptides with overlapping allowed. NetCTL predicts CTL epitopes restricted to 12 MHC class I supertypes and a specificity of 97% was used. MHC-II was used with an epitope length of 15 residues against 14 HLA-DR alleles covering the nine HLA-DR, six HLA-DQ and six HLA-DP supertypes.

Plasmid pVAX1™ was obtained from Invitrogen/Life Technologies (New York, USA). For this and related studies, large candidates were subdivided in coding sequences (CDS) of maximum 1000 bp in length. For the high priority pool, candidates 31, 56, and 12 were selected. The candidate 56 (EscC) was divided in 2 CDS. As the amino terminal portion of EscC is oriented towards the periplasm (Spreter et al., 2009 *Nat Struct Mol Biol* 16:468-76), the fragment comprising the carboxy-terminus (pVAX56.2) was selected for testing. Candidates 43, 16, and 9 were selected for medium priority pool. Finally, candidate 51 and two CDS of the candidate 49 for the low priority pool were selected. The CDS for selected candidates were amplified by PCR from genomic DNA of *E. coli* EDL933 (O157:H7) using the corresponding forward (Fw) and reverse (Rv) primers containing HindIII and XhoI restriction sites, respectively (Table 3). The resulting fragments were digested and cloned into the HindIII and XhoI sites of pVAX 1. Fw primers were

TABLE 2

Overview of prediction programs used.

| | Physicochemical properties | | | | Immunological properties | | |
|---|---|---|---|---|---|---|---|
| | Transmembrane (TM)* | Signal-peptide (SP) | Sub-cellular localization | Adhesion Probability* | B-cell epitopes | T-cell epitopes | Antigenicity |
| 1 | TMHMM | Signal-P (trained on Gram negative bacteria) | Signal-P (trained on Gram negative bacteria) | SPAAN | ABCPred (linear) | NetCTL (MHC-I) | VaxiJen |
| 2 | HMMTOP | PsortB | PsortB | LipoP | | NetMHCII (MHC-II) | |
| 3 | PHOBIUS | NetChop | NetChop | Lipo | | | |

*Consensus of results from all programs in a given category, wherever applied.

The transmembrane (TM) regions were predicted using TMHMM (Krogh et al., 2001 *J Mol Biol* 305:567-80), HMMTOP (Tusnady and Simon, 2001 *Bioinformatics* 17:849-50) and Phobius (Kall et al., 2007 *Nucleic Acids Res* 35:W429-432). Phobius can discern TM topology and signaling peptide in a protein. It substantially reduces the errors in the predictions of these two characteristics when compared to other algorithms including TMHMM. After an designed to generate a Kozak consensus sequence (ACCATGG) at the 5' end of each CDS. All of the clones were sequenced.

TABLE 3

Primers used for plasmid construction.

| Construct | EHEC gene insert | Primers | Sequence 5'-3' |
|---|---|---|---|
| pVAX-12 | Z1538 | PVAX12-Fw | ACCAAGCTTACCATGGTTTCTACTTTCAAAAAAGCAG (SEQ ID NO: 4) |
| | | PVAX12-Rv | ACCCTCGAGTAGAGGTAGCTCAGGGTGTATTCT (SEQ ID NO: 5) |
| pVAX-31 | Z3075 | PVAX31-Fw | ATTAAGCTTACCATGGGTAAACTTTATGCCGCCATTTTG (SEQ ID NO: 6) |
| | | PVAX31-Rv | ATTCTCGAGTCAATGATGATGATGATGATGGAACTTATAACCGACACCCAC (SEQ ID NO: 7) |
| pVAX-56.2 | a.a. 253-512 escC | PVAX56.2-Fw | ACCAAGCTTACCATGGACCGCGAAATAACGATGGAT (SEQ ID NO: 8) |
| | | PVAX56.2Rv | ACCCTCGAGTTATTCGCTAGATGCAGATTTTATC (SEQ ID NO: 9) |
| pVAX-43 | Z4321 | PVAX43-Fw | ATTAAGCTTACCATGGGTGGTTCAAGACTGGCTGATAATC (SEQ ID NO: 10) |
| | | PVAX43-Rv | ATTCTCGAGTTAAAAACGATAACCAACTCCAAC (SEQ ID NO: 11) |
| pVAX-16 | Z1908 | PVAX16-Fw | ATTAAGCTTACCATGGCTTTTTCTTTTTTTTCTACAAAACCCATACC (SEQ ID NO: 12) |
| | | PVAX16-Rv | ATTCTCGAGTTATCCGCCCGCACCATTAACC (SEQ ID NO: 13) |
| pVAX-9 | Z0981 | PVAX9-Fw | ACCAAGCTTACCATGGGTAAAGTTTGTGCAGCAA (SEQ ID NO: 14) |
| | | PVAX9-Rw | ACCCTCGAGTCAAAATTTATAACCGACACCCAC (SEQ ID NO: 15) |
| pVAX-51 | espB | PVAX51-Fw | ATTAAGCTTACCATGGATACTATTGATAATACTCAAG (SEQ ID NO: 16) |
| | | PVAX51-Rv | ATTCTCGAGTCAATGATGATGATGATGATGCCCAGCTAAGCGACCCGATTG (SEQ ID NO: 17) |
| pVAX-49.1 | a.a. 641-960 ehaG | PVAX49.1-Fw | ACCAAGCTTACCATGGCCGATGCCGTTAACGGCTC (SEQ ID NO: 18) |
| | | PVAX49.2-Rv | TTATCTAGACTCGAGTTACTCGGCGTTCGCAATGGTG (SEQ ID NO: 19) |
| pVAX-49.2 | a.a. 1141-1380 ehaG | PVAX49.2-Fw | ACCAAGCTTACCATGGAACTGCTCGGTGCATTGTCT (SEQ ID NO: 20) |
| | | PVAX49.2-Rv | TTATCTAGACTCGAGTTAGCCGGAACCAATCGCGACG (SEQ ID NO: 21) |

Six to eight week-old female BALB/c mice (Harlan Laboratories) were divided into six groups (n=10). Mice were immunized intranasally with 20 μg of the DNA vaccines in Tris-EDTA (TE) buffer (10 μl in each nostril), arranged as followed: (1) Tris-EDTA (TE) buffer only, (2) TE plus cholera toxin (CT, adjuvant), (3) pVAX vector plus CT, (4) pVAX-High Priority (HP), (5) pVAX-Medium Priority (MP), and (6) pVAX-Low Priority (LP) vaccine candidates. All the vaccine candidates were administered in pools of 3 targets (20 μg of each plasmid) along with the adjuvant CT (1 μg/μl). For the immunization, the animals were anesthetized with isoflurane and primed with final dose of 60 μg of DNA per mice followed by 2 and 4 weeks boosts using same dose without CT. In the case of the individual candidate immunizations, the animals received a total of 60 μg of individual plasmid. In CT control group, priming was with CT followed by TE boosts. One week after the last boost, blood and fecal samples were collected to monitor mucosal antibody response.

To determine the protective ability of the potential DNA vaccine candidates, all immunized mice were challenged with a dose of $5\times10^9$ CFU of the streptomycin resistant EHEC O157:H7 strain 86-24, via gavage, two weeks after the last boost. Two hours prior to the challenge, mice received an i.p. dose of cimetidine hydroxyzine (10 mg/ml) to reduce stomach's acidity. Fecal samples were collected from each group at indicated days after infection. Stools were dissolved in 2 ml of PBS, serially diluted and plated. To recover bacteria from the intestine, the mice were euthanized at indicated days and ceca were excised and homogenized in 2 ml of PBS. Bacterial suspensions were serially-diluted and plated. Both organ and fecal samples were plated on MacConkey agar plates containing streptomycin and then incubated at 37° C. overnight prior to *E. coli* O157:H7 colonies enumeration.

Sera were obtained by retro-orbital bleeding, clotting whole blood for 30 min at room temperature and centrifugation at 3,000×g for 15 min at 4° C. The resulting supernatant was collected and used for ELISA. For sIgA measurement, feces were weighted and diluted to 1 g/ml with PBS-PM SF. After vigorous homogenization with vortex, feces were incubated for 1 h on ice and centrifuged at 4000 rpm for 30 min at 4° C. The supernatant was collected and stored at −20° C. prior to use.

Total serum IgG antibody responses were determined by ELISA according to manufacturer's instructions (ebiosciences). Briefly, polystyrene 96-well high binding ELISA plates (Nunc, Denmark) were coated overnight at 4° C. with capture IgG antibody. The plates were washed thrice in PBS containing 0.05% Tween 20 (v/v) (PBS-T) and plated with blocking buffer. The diluted serum sample (1:1000 and 1:10,000) and IgG standard of known activity were incubated, followed by repeated washing with 0.05% PBS-T. Next, horseradish peroxidase goat anti-mouse IgG in PBS-T (1:250) was added to the ELISA plates and incubated at 37° C. for 30 min followed by washing. One hundred μl of tetramethylbenzidine (TMB) were added to the cells and incubated at room temperature for 15 min. The reaction was stopped with 100 μl of 2 M $H_2SO_4$ and the $OD_{450}$ was determined.

For EHEC specific antibody response, wild-type EHEC O157:H7 were grown overnight in LB broth. Bacterial cells were pelleted (15 min at 5,000×g) and re-suspended in PBS. The bacterial suspension was pulse-sonicated on ice for 5 min. The sonicated sample was centrifuged (10,000×g for 15 min at 4° C.) and total protein concentration in the supernatant was determined by the bicinchoninic acid protein (BCA) assay. For ELISA, polystyrene 96 well Nunc plates were coated overnight at 4° C. with 100 μl of EHEC extract (2 μg/ml in coating buffer) and followed the procedure described above.

The cytokine levels in serum and feces from immunized and non-immunized mice were measured on a Bio-Plex 200 system powered by Luminex xMAP technology (Bio-Rad, USA) using a specific 23 panel group mouse assay kits (Cat. No. M60009RDPD), following manufacturer's instructions. The cytokines, chemokines, and growth factors include: IL-1α, IL-1β, IL-2, IL-3, IL-4, IL-5, IL-6, IL-9, IL-10, IL-12 (p40), IL-12p70, IL-13, IL-17, TNF-α, IFN-γ, MIP-1α, MIP-1β, KC, eotaxin, MCP-1, G-CSF, GM-CSF and RANTES. A heatmap of a normalized matrix was created that correlates cytokine response pattern to stimulation by high priority vaccine candidates. For each cytokine, mean and standard deviation were calculated from their induction values (pg/ml) across the three candidates and were normalized to controls (TE and pVAX-1). The Z-score transformation was calculated for each cytokine by subtracting each induction value from the row mean and dividing by the row standard deviation (Kalita et al., 2013 *Biomed Res Int* 2013:1-17). Overall, the Z-score gives an estimation of the deviation of the measurement from the row mean in standard deviation units. Each block of red or green represents a high positive or negative correlation between the cytokine production and the vaccine candidate under investigation.

All the statistical significance between control and vaccinated groups was assessed using SPSS software. One way ANOVA and Student's t-test with threshold of $P<0.05$ was used to analyze the data for colonization and antibody response.

II. Vaccine Compositions

Vaccine compositions described herein may include adjuvants to further increase the immunogenicity of one or more of the EHEC antigens. Such adjuvants include any compound or compounds that act to increase an immune response to an EHEC antigen or combination of antigens, thus reducing the quantity of antigen necessary in the vaccine, and/or the frequency of injection necessary in order to generate an adequate immune response. Adjuvants may include for example, emulsifiers, muramyl dipeptides, avridine, aqueous adjuvants such as aluminum hydroxide, chitosan-based adjuvants, and any of the various saponins, oils, and other substances known in the art, such as Amphigen, LPS, bacterial cell wall extracts, bacterial DNA, synthetic oligonucleotides and combinations thereof (Schijns et al., 2000 *Curr. Opi. Immunol.* 12:456), *Mycobacterial phlei* (*M. phlei*) cell wall extract (MCWE) (U.S. Pat. No. 4,744,984), *M. phlei* DNA (M-DNA), M-DNA-*M. phlei* cell wall complex (MCC). For example, compounds which may serve as emulsifiers herein include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids (i.e., metallic soaps), and organic sulfonates such as sodium lauryl sulfate. Synthetic cationic agents include, for example, cetyltrimethylammonium bromide, while synthetic nonionic agents are exemplified by glyceryl esters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil may be a mineral oil, a vegetable oil, or an animal oil. Mineral oil, or oil-in-water emulsions in which the oil component is mineral oil are preferred. In this regard, a "mineral oil" is defined herein as a mixture of liquid hydrocarbons obtained from petrolatum via a distillation technique; the term is synonymous with "liquid paraffin," "liquid petrolatum" and "white mineral oil." The term is also intended to include "light mineral oil," i.e., an oil which is similarly obtained by distillation of petrolatum, but which has a slightly lower specific gravity than white mineral oil. A particularly preferred oil component is the oil-in-water emulsion sold under the trade name of EMULSIGEN PLUS™ (comprising a light mineral oil as well as 0.05% formalin, and 30 mcg/mL gentamicin as preservatives), available from MVP Laboratories, Ralston, Nebr. Suitable animal oils include, for example, cod liver oil, halibut oil, menhaden oil, orange roughy oil and shark liver oil, all of which are available commercially. Suitable vegetable oils, include, without limitation, canola oil, almond oil, cottonseed oil, corn oil, olive oil, peanut oil, safflower oil, sesame oil, soybean oil, and the like.

Alternatively, a number of aliphatic nitrogenous bases can be used as adjuvants with the vaccine formulations. For example, known immunologic adjuvants include amines, quaternary ammonium compounds, guanidines, benzamidines, and thiouroniums (Gall, 1966 *Immunology* 11:369-86). Specific compounds include dimethyldioctadecylammonium bromide (DDA) (available from Kodak) and N,N-dioctadecyl-N,N-bis(2-hydroxyethyl)propanediarnine ("avridine").

The compositions of the present invention are normally prepared as injectables, either as liquid solutions or suspensions, or as solid forms which are suitable for solution or suspension in liquid vehicles prior to injection. The preparation may also be prepared in solid form, emulsified or the active ingredient encapsulated in liposome vehicles or other particulate carriers used for sustained delivery. For example, the vaccine may be in the form of an oil emulsion, water in oil emulsion, water-in-oil-in-water emulsion, site-specific emulsion, long-residence emulsion, sticky-emulsion, microemulsion, nanoemulsion, liposome, microparticle, microsphere, nanosphere, nanoparticle, and various natural or synthetic polymers, such as nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures, that allow for sustained release of the vaccine.

Furthermore, the polypeptides may be formulated into compositions in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Actual methods of preparing such dosage forms are known, or will be apparent, to those skilled in the art. See, e.g., Remington's Pharmaceutical Sciences, Mack Publishing Company, Easton, Pa., 18th edition, 1990.

The composition is formulated to contain an effective amount of EHEC antigen(s) described herein, the exact amount being readily determined by one skilled in the art, wherein the amount depends on the animal to be treated and the capacity of the animal's immune system to synthesize antibodies. The composition or formulation to be administered will contain a quantity of one or more EHEC antigens adequate to achieve the desired state in the subject being treated. For purposes of the present invention, a therapeutically effective amount of a vaccine comprising EHEC antigens, contains about 0.05 to 1500 μg EHEC protein, preferably about 10 to 1000 μg EHEC protein, more preferably about 30 to 500 μg and most preferably about 40 to 300 μg, or any integer between these values.

Routes of administration include, but are not limited to, nasal, oral, topical, subcutaneous, intramuscular, intravenous, subcutaneous, intradermal, transdermal, and subdermal. Depending on the route of administration, the volume per dose is preferably about 0.001 to 10 ml, more preferably about 0.01 to 5 ml, and most preferably about 0.1 to 3 ml. Vaccines can be administered in a single dose treatment or in multiple dose treatments (boosts) on a schedule and over a time period appropriate to the age, weight, and condition of the subject, the particular vaccine formulation used, and the route of administration.

Any suitable pharmaceutical delivery means may be employed to deliver the compositions to the vertebrate subject. For example, inhalers, instillation devices, conventional needle syringes, spring or compressed gas (air) injectors, liquid jet injectors, and particle injectors are all appropriate for delivery of the compositions.

III. Proteinaceous Compositions

Proteinaceous compositions of the invention include polypeptides and polypeptide segments of proteins encoded by the nucleic acids corresponding to the EHEC nucleic acids described herein. In certain embodiments, antigens can be engineered to include polypeptide variants of the antigens corresponding to the antigens described herein. As used herein, a "protein" or "polypeptide" refers to a polymer of amino acid residues. In some embodiments, a wild-type version of a protein or polypeptide are employed, however, in many embodiments, all or part of an antigen or polypeptide is absent or altered.

A "modified protein" or "modified polypeptide" or "variant protein" or "variant polypeptide" refers to a protein or polypeptide whose chemical structure or amino acid sequence is altered with respect to the wild-type or a reference protein or polypeptide. In some embodiments, a modified protein or polypeptide has at least one modified activity or function (recognizing that proteins or polypeptides may have multiple activities or functions). The modified activity or function may be reduced, diminished, eliminated, enhanced, improved, or altered in some other way with respect to that activity or function in a wild-type protein or polypeptide. It is contemplated that a modified protein or polypeptide may be altered with respect to one activity or function yet retain wild-type or unaltered activity or function in other respects.

It is contemplated that polypeptides may be modified by truncation, rendering them shorter than their corresponding unaltered form or by fusion or domain shuffling which may render the altered protein longer.

Amino acid sequence variants of the polypeptides of the present invention can be substitutional, insertional, or deletion variants. A mutation in a gene encoding a polypeptide may affect 1, 2, 3, 4, 5, 6, 7, 8, 9, 10, 15, 20, 25, 30, 40, 50, 60, 70, 80, 90, 100 or more non-contiguous or contiguous amino acids (i.e., segment) of a polypeptide, as compared to a wild-type or unaltered polypeptide or other reference polypeptide.

Deletion variants lack one or more residues of the native, unaltered, or wild-type protein. Individual residues can be deleted, or all or part of a domain (such as a catalytic or binding domain) can be deleted. Insertional mutants typically involve the addition of material at a non-terminal point in the polypeptide; a specific type of insert is a chimeric polypeptide that includes homologous or similar portions of a related protein in place of the related portion of a target protein. This may include the insertion of an immunoreactive epitope or simply one or more residues. Terminal additions, typically called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The term "functionally equivalent codon" is used herein to refer to codons that encode the same amino acid, such as the six codons for arginine or serine, and also refers to codons that encode biologically equivalent amino acids. Amino acids codons include: Alanine (Ala, A) GCA, GCC, GCG, or GCU; Cysteine (Cys, C) UGC or UGU; Aspartic acid (Asp, D) GAC or GAU; Glutamic acid (Glu, E) GAA or GAG; Phenylalanine (Phe, F) UUC or UUU; Glycine (Gly, G) GGA, GGC, GGG or GGU; Histidine (His, H) CAC or CAU; Isoleucine (Ile, I) AUA, AUC, or AUU; Lysine (Lys, K) AAA or AAG; Leucine (Leu, L) UUA, UUG, CUA, CUC, CUG, or CUU; Methionine (Met, M) AUG; Asparagine (Asn, N) AAC or AAU; Proline (Pro, P) CCA, CCC, CCG, or CCU; Glutamine (Gln, Q) CAA or CAG; Arginine (Arg, R) AGA, AGG, CGA, CGC, CGG, or CGU; Serine (Ser, S) AGC, AGU, UCA, UCC, UCG, or UCU; Threonine (Thr, T) ACA, ACC, ACG, or ACU; Valine (Val, V) GUA, GUC, GUG, or GUU; Tryptophan (Trp, W) UGG; and Tyrosine (Tyr, Y) UAC or UAU.

It also will be understood that amino acid and nucleic acid sequences may include additional residues, such as additional N- or C-terminal amino acids, or 5' or 3' sequences, and yet still be essentially as set forth herein, including having a certain biological activity. The addition of terminal sequences particularly applies to nucleic acid sequences that may, for example, include various non-coding sequences flanking either the 5' or 3' portions of the coding region or may include various internal sequences, i.e., introns, which are known to occur within genes.

The following is a discussion based upon changing of the amino acids of a protein described herein to create an equivalent, or even an improved, molecule. For example, certain amino acids may be substituted for other amino acids in a protein structure without appreciable loss of interactive binding capacity with structures such as, for example, antigen-binding regions of antibodies or binding sites on receptor molecules. Since it is the interactive capacity and nature of a protein that defines that protein's biological functional activity, certain amino acid substitutions can be made in a protein sequence, and in its underlying polynucleotide sequence, and nevertheless produce a protein with like properties. It is thus contemplated by the inventors that various changes may be made in the nucleic acid sequences of the antigens described herein without appreciable loss of biological utility or activity of interest. In certain aspects the nucleic acid can be divided into segments encoding fragments of a parent polypeptide that retain antigenicity.

In making such changes, the hydropathic index of amino acids may be considered. The importance of the hydropathic amino acid index in conferring a biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

IV. Nucleic Acid Molecules

Certain embodiments are directed to compositions and methods that include polynucleotides that are capable of expressing all or part of an antigenic protein or polypeptide described herein or discoverable through the described methods. The polynucleotides may encode a peptide or polypeptide containing all or part of a antigenic amino acid sequence.

As used herein, the term an isolated "RNA, DNA, or nucleic acid segment" refers to a RNA, DNA, or nucleic acid molecule that has been isolated from total genomic DNA or other contaminants. In certain embodiments the polynucleotide has been isolated free of other nucleic acids.

The term "complementary DNA" or "cDNA" refers to DNA prepared using RNA as a template. There may be times when the full or partial genomic sequence is preferred.

Similarly, a polynucleotide encoding a polypeptide refers to a nucleic acid segment including coding sequences and, in certain aspects, regulatory sequences, isolated substantially away from other naturally occurring genes or protein encoding sequences. In this respect, the term "gene" is used for simplicity to refer to a nucleic acid unit encoding a protein, polypeptide, or peptide (including any sequences required for proper transcription, post-translational modification, or localization). As will be understood by those in the art, this functional term includes genomic sequences, cDNA sequences, and smaller engineered nucleic acid segments that express, or may be adapted to express, proteins, polypeptides, domains, peptides, fusion proteins, and mutants.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol.

It is contemplated that the nucleic acid constructs of the present invention may encode full-length polypeptide(s) from any source or encode a truncated or modified version of the polypeptide(s). A nucleic acid sequence may encode a full-length polypeptide sequence with additional heterologous coding sequences, for example to allow for purification of the polypeptide, transport, secretion, post-translational modification, or for therapeutic benefits such as targeting or efficacy. A tag or other heterologous polypeptide may be added to a polypeptide-encoding sequence. The term "heterologous" refers to a polypeptide, polynucleotide, or segment thereof that is not the same as the modified polypeptide, polynucleotide, or found associated with or encoded by the naturally occurring bacteria.

The nucleic acid segments used in the present invention encompass modified nucleic acids that encode modified polypeptides. Such sequences may arise as a consequence of codon redundancy and functional equivalency. Functionally equivalent proteins or peptides may be created via the application of recombinant DNA technology, in which changes in the protein structure may be engineered, based on considerations of the properties of the amino acids being exchanged. Changes designed by humans may be introduced through the application of site-directed mutagenesis techniques, e.g., to introduce improvements to the antigenicity.

In certain other embodiments, the invention concerns isolated nucleic acid segments and recombinant vectors that include within their sequence a contiguous nucleic acid sequence from that shown in sequences identified herein (and/or incorporated by reference). In various embodiments, the polynucleotide may be altered or mutated. Alterations or mutations may include insertions, deletions, substitutions, rearrangement, inversions. Mutation is the process whereby changes occur in the function or structure of a molecule. Mutation can involve modification of the nucleotide sequence of a gene or coding region. Changes in single genes may be the consequence of point mutations that involve the removal, addition, or substitution of a single nucleotide base within a DNA sequence, or they may be the consequence of changes involving the insertion or deletion of large numbers of nucleotides.

Insertional mutagenesis is based on the modification of a gene via insertion of a known nucleotide or nucleic acid fragment. Insertional mutagenesis may be accomplished using standard molecular biology techniques.

The term “expression vector” refers to a vector containing a nucleic acid sequence coding for at least part of a gene product capable of being transcribed. In some cases, RNA molecules are translated into a protein, polypeptide, or peptide. Expression vectors can contain a variety of “control sequences,” which refer to nucleic acid sequences necessary for the transcription and possibly translation of an operably linked coding sequence in a particular host organism. In certain embodiments an expression vector is pVAX vector.

A “promoter” is a control sequence that is a region of a nucleic acid sequence at which initiation and rate of transcription are controlled. It may contain genetic elements that bind regulatory proteins and molecules, such as RNA polymerase and other transcription factors. The phrases “operatively positioned,” “operatively coupled,” “operatively linked,” “under control,” and “under transcriptional control” mean that a promoter is in a correct functional location and/or orientation in relation to a nucleic acid sequence to control transcriptional initiation and/or expression of that sequence. A promoter may or may not be used in conjunction with an “enhancer,” which refers to a cis-acting regulatory sequence involved in the transcriptional activation of a nucleic acid sequence.

A specific initiation signal also may be required for efficient translation of coding sequences. These signals include the ATG initiation codon or adjacent sequences. Heterologous translational control signals, including the ATG initiation codon, may need to be provided. The translational control signal and initiation codons can be either natural or synthetic. The efficiency of expression may be enhanced by the inclusion of appropriate transcription enhancer elements.

Vectors can include a multiple cloning site (MCS), which is a nucleic acid region that contains multiple restriction enzyme sites any of which can be used in conjunction with standard recombinant technology to digest the vector. A vector can be linearized or fragmented using a restriction enzyme that cuts within the MCS to enable heterologous sequences to be ligated to the vector.

The vectors or constructs can comprise at least one termination signal. A “termination signal” or “terminator” is comprised of the nucleic acid sequences involved in specific termination of an RNA transcript by an RNA polymerase. Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator.

A polyadenylation signal can be used to effect proper polyadenylation of a transcript. The nature of the polyadenylation signal is not believed to be crucial to the successful practice of the invention. Embodiments include the SV40 polyadenylation signal and/or the bovine growth hormone polyadenylation signal.

V. Kits Related to Ehec Antigens

In still another embodiment, the present invention provides a pharmaceutical kit for ready administration of an immunogenic, prophylactic, or therapeutic regimen. This kit is designed for use in a method of inducing a high level of antigen-specific immune response in a mammalian or vertebrate subject. The kit may contain at least one immunogenic composition comprising an antigenic composition as described herein. For example, multiple prepackaged dosages of the immunogenic composition or a DNA vector encoding antigens are provided in the kit for multiple administrations. The kit may also contain at least one immunogenic composition comprising an EHEC immunogenic composition as described herein. In one embodiment, multiple prepackaged dosages of the expression vectors and/or immunogenic composition are provided in the kit for multiple administrations.

The kit also contains instructions for using the immunogenic compositions in a prime/boost method as described herein. The kits may also include instructions for performing certain assays, various carriers, excipients, diluents, adjuvants and the like above-described, as well as apparatus for administration of the compositions, such as syringes, electroporation devices, spray devices, etc. Other components may include disposable gloves, decontamination instructions, applicator sticks or containers, among other compositions.

VI. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

From in Silico Protein Epitope Density Prediction to Testing *Escherichia Coli* O157:H7 Vaccine Candidates in a Murnine Model of Colonization A. Results Clustering of Vaccine Candidates by Immunoinformatic Analysis.

Figure 2:
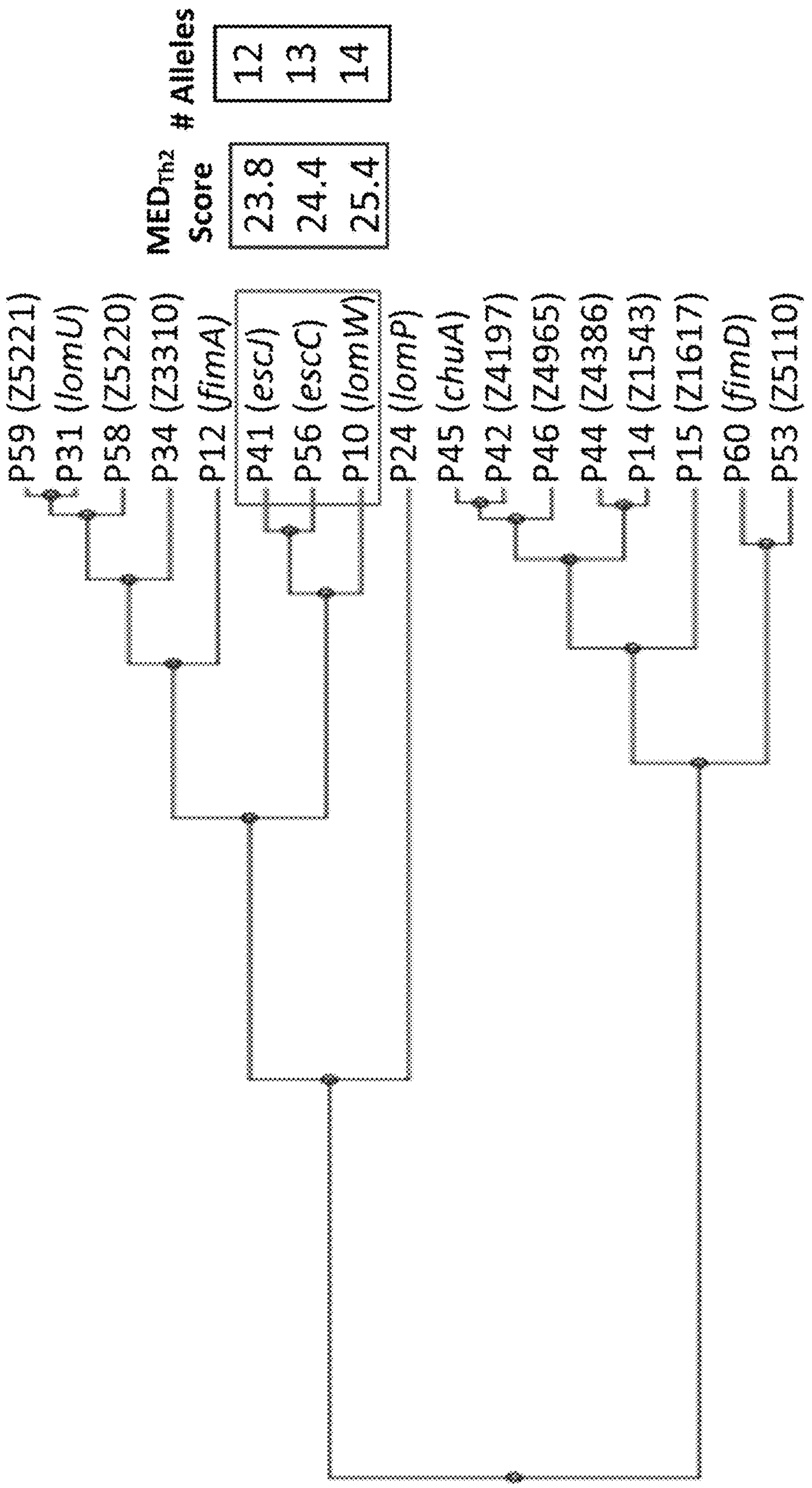
FIG. 2. Dendrogram of Vaccine Candidates. Clustering of candidates based on Mature Epitope Density (MED) Score. Selected candidates (green), their compiled $MED_{Th2}$ score (red) and the number of HLA alleles covered based (black) are highlighted.

FIG. 1A provides a schematic representation of Th2-oriented epitope prediction and selection of seventeen, potentially protective, high-priority (HP) vaccine candidates in EHEC O157:H7 (Garcia-Angulo et al., 2014, *Infect Immun* 82:2016-26). The distribution of high-binding epitopes across numerous HLA alleles is depicted in a heatmap. This heatmap highlights allele coverage, with proteins exhibiting increased allele coverage, and thus more likely to induce an effective immune response in a heterogenous population. While the majority of high priority (HP) proteins have high $MED_{Th2}$ scores (above 10, FIG. 1B), there is selective binding across the array of HLA alleles. For example, while lomW showed a high predictive binding affinity towards DQ5 and DRB6 alleles, the escJ epitopes may bind more strongly to DP4 as compared to other gene products. The data in FIG. 1B was used to derive a dendrogram (FIG. 2) to further highlight protein clustering based on $MED_{Th2}$ score. Based on previous studies that tested a pool of three randomly selected HP candidates, immunization with truncated escC resulted in the most significant reduction in bacterial colonization. However, that study utilized only the second half of the gene as a vaccine target instead of the entire gene, because there were problems in the cloning process. In the present study, the full-length escC gene was successfully cloned. The goal of this study was to examine the protective capacity of whole escC gene together with two closely related genes (lomW and escJ). In summary, candidates were selected based on $MED_{Th2}$ scores, allele coverage, physiochemical features, and predicted function.

Bacterial Colonization in Immunized Mice with DNA Vaccine.

Figures 3A, 3B:
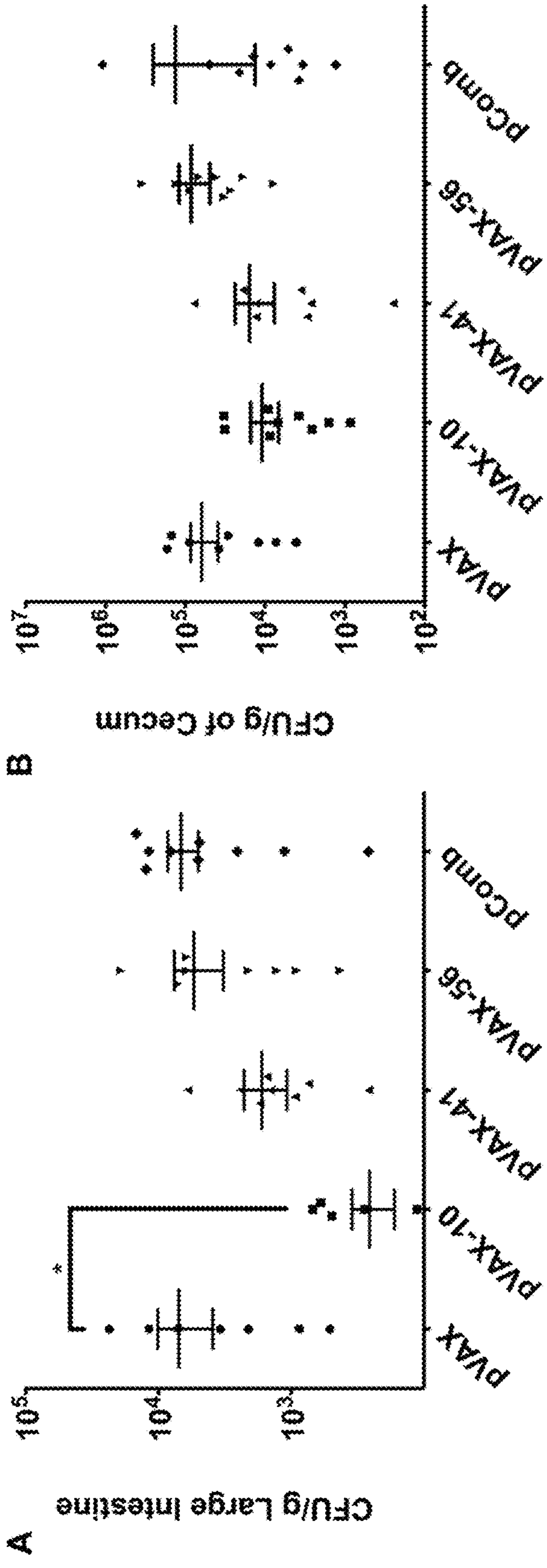
FIGS. 3A-3B. Bacterial counts in infected mice with EHEC O157:117. Bacterial colonization of large intestine (A) and cecum (B) segments as collected from mice vaccinated with pVAX1, lomW (pVAX-10), escJ (pVAX-41), escC (pVAX-56), and pComb followed by challenge with $5\times10^9$ CFU of EHEC O157:H7. Bacterial counts are represented as CFU per gram of tissue. Means±the SEM of the CFU/g from 10 mice presented and an asterisk (*) indicates statistical significance as defined ($p<0.05$).

BALB/c mice were immunized with the DNA vaccine candidates as described in Material and Methods. Two weeks after the last immunization, animals were challenged with a dose of $5\times10^9$ CFU of streptomycin-resistant *E. coli* O157:H7 strain 86-24 via gavage. Seven days post-challenge, large intestines and ceca were collected to enumerate bacterial colonization. The bacterial load in the gastrointestinal tract (FIG. 3) indicates bacterial reduction in mice immunized with the three tested candidate groups lomW (pVAX-10), escJ (pVAX-41), escC (pVAX-56) compared to pVAX-only immunized group. When a combination of all three (pComb) candidates were administered, the reduction in colonization was minimum. Immunization with lomW (pVAX-10) resulted in the greatest reduction in bacterial colonization in the large intestine (p=0.0423) (FIG. 3A). A similar trend is observed in cecum colonization, despite no statistical significance (FIG. 3B).

Immune Response of Mice Receiving the DNA Vaccine.

Figures 4A, 4B:
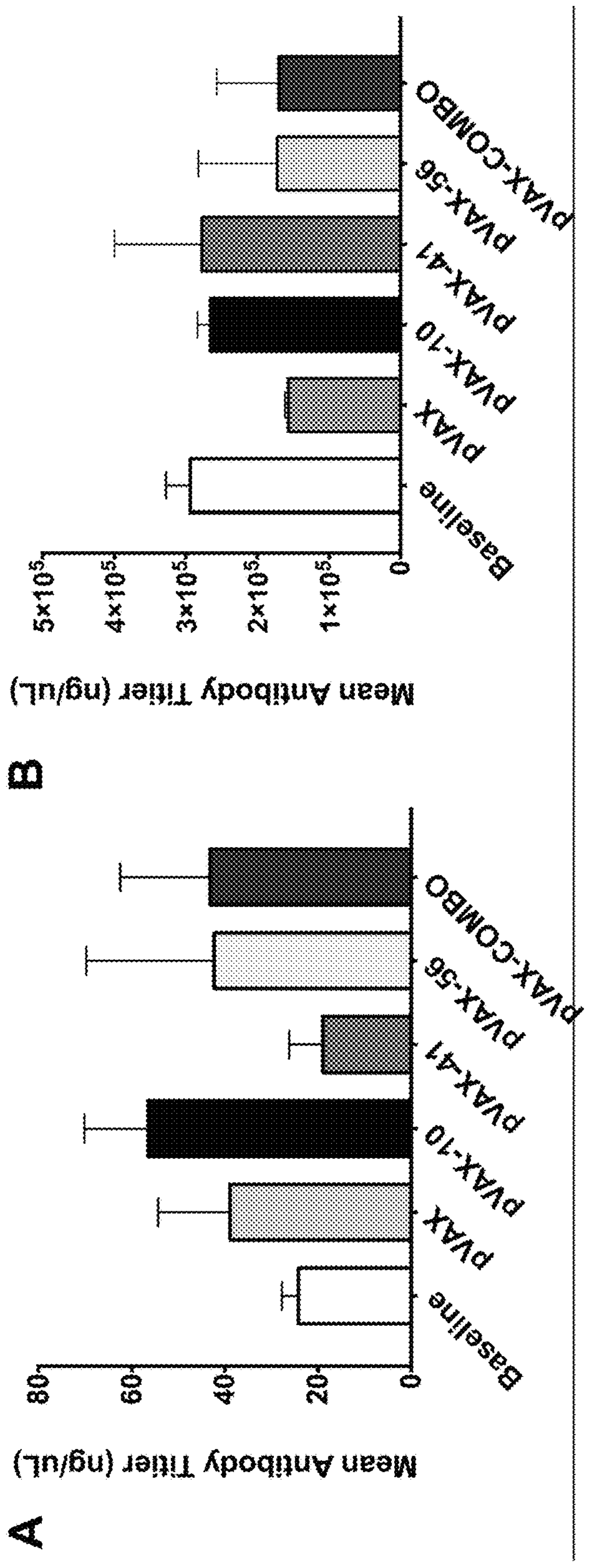
FIGS. 4A-4B. Immune response from mice immunized with pVAX candidates. Graphs show secreted immunoglobulin A (A) and IgG (B) total levels, two weeks after last immunization. Mean IgA levels were measured from fecal samples of three immunized mice with lomW (pVAX-10), escJ (pVAX-41), escC (pVAX-56), or pComb. Feces collected prior to immunization (baseline) and of mice immunized with pVAX1 were used as controls. The results are expressed as means±the SEM of triplicate values obtained from three mice from each group. Statistical significance was defined as ($p<0.05$). (B) Sera collected from mice immunized with vaccine candidates was used to measure total IgG antibodies by ELISA. The results are expressed as means±of the SEM of triplicate values from three mice in each group.

Fecal samples collected two weeks post-immunization were used to measure sIgA production. Mice immunized with lomW produced the highest levels of total sIgA when compared to unimmunized mice (baseline), mice immunized with pVAX1 alone, or any of the other immunization groups, though no statistical significance was observed (FIG. 4A). Similarly, escC was also shown to induce increased sIgA production. Furthermore, sera collected from immunized mice two weeks after the last immunization was used to measure total IgG antibodies. Unlike sIgA, there appears to be no observable differences in immunoglobulin production between the immunization groups (FIG. 4B).

Bacterial Adherence Inhibition by Sera.

Figures 5A, 5B:
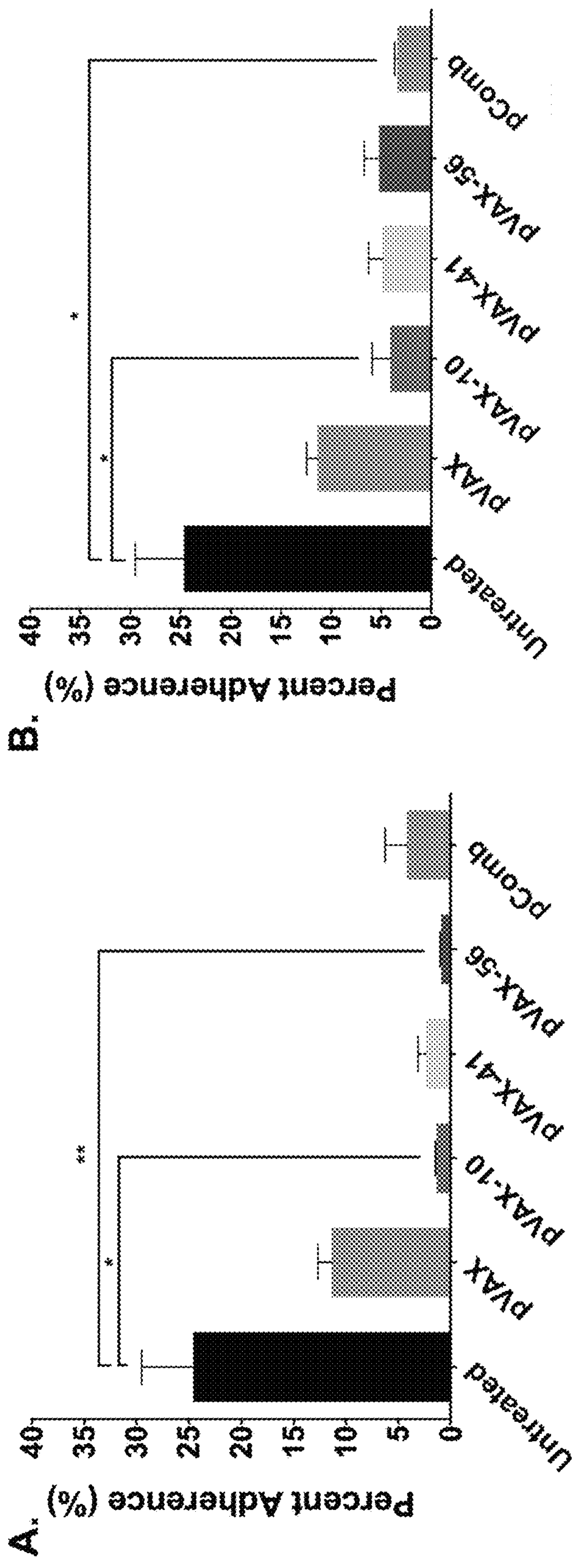
FIGS. 5A-5B. Bacterial adhesion reduction by immune sera from vaccinated mice. EHEC O157:H7 serotype EDL933 was incubated with 10% (A) or 5% (B) pooled sera (n=3) from immunized mice with lomW (pVAX-10), escJ (pVAX-41), escC (pVAX-56), and -pComb in PBS and further incubated with Caco-2 cells at an MOI of 1:100 for 3 hours to allow adherence. Sera from pVAX1 immunized mice as well as bacteria alone served as control groups. Bacterial adherence is shown as a percentage of bacteria recovered after incubation. Results are shown as percent adherence and as means±of the SEM of triplicate values obtained from individual incubation well of bacteria with Caco-2 cells, and an asterisk (*) indicates statistical significance as defined ($p<0.05$).

To further characterize the antibodies produced after vaccination, the capacity of immune sera to prevent the adherence in vitro of *E. coli* O157:H7 to human intestinal epithelial cells (Caco-2) was analyzed. Wild-type*E. coli* O157:H7 strain EDL933 was incubated with pooled sera (n=3) from immunized mice (5% and 10% concentration) at an MOI of 100 prior to infection of Caco-2 cells. It was observed that the most significant reduction in bacterial adherence from lomW (p=0.0466) and escC (p=0.0029) immunized mice sera at 10%, and from lomW (p=0.0466) and pComb (p=0.0143) at 5% concentration (FIGS. 5A and 5B). A decrease in the percent bacterial adherence from all groups at 5% compared to 10% sera was observed. Also, a reduction in bacterial adherence by sera from escJ and pComb compared to control groups at both concentrations was seen, but this reduction did not reach statistical significance (FIGS. 5A and 5B). The ability of sera to inhibit bacterial adherence in vitro to intestinal epithelial cells suggest the possibility of some specificity of the sera while recognizing surface-exposed proteins present on EHEC O157:H7 wild-type strain EDL933.

B. Materials and Methods

All manipulations of *E. coli* strains were conducted in approved and certified Biosafety Level 2 facilities at the University of Texas Medical Branch (UTMB), and experiments were performed in accordance with standard operating practices. The animal studies were carried out in strict accordance with the recommendations in the Guide for the Care and Use of Laboratory Animals of the National Institutes of Health. The protocol (IACUC #0709042B) was approved by the Institution for Animal Care and Use Committee at UTMB.

Bacterial Strains Culture Conditions.

All bacterial strains used in this study were stored in 50% glycerol at −80° C. Liquid cultures were generated by inoculating Luria-Bertani (LB) broth, with or without 50 μg/mL streptomycin. Liquid cultures were grown overnight at 37° C. with agitation. The prototypical *E. coli* O157:H7 strain 86-24 was used for animal challenge studies. *E. coli* O157:H7 wildtype strain EDL933 was utilized for gene amplifications and bacterial adhesion assays. *E. coli* strain DH5α (Life Technologies) was used for propagation of strains bearing pVAX1 plasmid and was routinely grown in LB broth and agar containing kanamycin (Sigma, 50 μg/mL) for plasmid selection.

Immunoinformatic Analysis.

NetMHC-II (Nielsen and Lund, 2009, *BMC Bioinformatics* 10:296), NetCTL (Larsen et al., 2007, *BMC Bioinformatics* 8:424), and ABCPred (Saha and Raghava, 2006, *Proteins* 65:40-48) were used to predict the WIC class II, MHC class I and linear B-cell binding epitopes, respectively, in EHEC O157:H7 specific proteins. Program outputs reported the binding affinity ($IC_{50}$) of individual epitopes to various HLA alleles. Based on these $IC_{50}$ values, all possible 9-mer epitopes from each protein were predicted as weak ($IC_{50}$>500 nM) or strong binding ($IC_{50}$>50 nM). Only strong binding peptides having a predicted $IC_{50}$ value less than 50 nM (used as threshold) were selected. To assess the potential to induce a Th2-skewed protective response, the inventor focused on NetMHCII output consisting of six HLA-DP, six HLA-DQ and 14 HLA-DR alleles. Two parameters were derived from the NetMHCII output: (a) average MHC Affinity (Avg-MA) for all epitopes in a given protein sequence and (b) mature epitope density ($MED_{Th2}$) score using the formula below, where epitope length is core 9-mer (Santos et al., 2013, *BMC Genomics* 14:Suppl 6:S4).

$$MED_{Th2} = \frac{\text{Predictions}}{\text{Chances}} = \frac{\text{number of predicted epitopes } X(50 - Avg\text{-}MA)}{\text{protein sequence length} - \text{epitope length}^* + 1}$$

This $MED_{Th2}$ score reflects aggregate T-cell (Th2) epitope content. Higher scores indicate a better prediction for the protective nature of the protein. Also, the number of alleles bound by each protein was evaluated in order to target a larger population coverage. A heatmap of Avg-MA against each HLA-allele for all protein sequences was generated. A clustered image map (CIM) of a normalized matrix was created that correlates Avg-MA of each allele to different proteins. For each protein, mean and standard deviation were calculated from their Avg-MA for all alleles. Z-score transformation was calculated for each of the alleles by subtracting each Avg-MA value by the row mean and dividing by the row standard deviation (Kalita et al., 2013, *Biomed Res Int* 2013:1-17). Hierarchical clustering of HP proteins was performed using an average-linkage clustering algorithm based on their $MED_{Th2}$ scores.

DNA Vaccine Construction.

Vaccine candidates were amplified from *E. coli* EDL933 genomic DNA. Forward (Fw) and reverse (Rv) primer sequences contained HindIII and XhoI restriction sites, respectively. The 5' end of Fw primers were designed with a Kozak consensus sequence (ACCATGG) to enhance transcription. Genes were amplified with Phusion® High Fidelity Polymerase (New England Biolabs) and ligated into the eukaryotic expression vector pVAX1 (Invitrogen, Life Technologies). Plasmids containing desired candidates were verified by directional sequencing and transformed into competent *E. coli* DH5α for propagation. For immunization studies, plasmids were purified using the Endotoxin-free Giga Kit (Qiagen) according to manufacturer's instructions. DNA samples were quantified using an Epoch Microplate Spectrophotometer (BioTek) and stored at −20° C.

Immunization and Sample Collection.

Six to eight-week-old female BALB/c mice were obtained from Charles River Laboratories and housed in a specific pathogen-free barrier under biosafety level 2 conditions and allowed to acclimate for 5 days prior to vaccination. Mice were divided into 5 groups (n=10 each), including pVAX (vector), lomW (pVAX-10), escJ (pVAX-41), escC (pVAX-56), and combination (pComb). Mice were anesthetized using isoflurane inhalation and administered a prime and two boosts (days 0, 14 and 28) intranasal (i.n.) immunization of approximately 60 μg DNA in Tris-EDTA. Prime vaccinations were administered along with Cholera Toxin (CT) as adjuvant (1 μg/uL). In the case of the combination vaccine, approximately 20 μg of each plasmid were mixed and administered as a single vaccine. Fecal and sera samples were collected prior to vaccination for determination of baseline antibody titers. Fecal samples were collected following final boost to monitor mucosal antibody titers. Briefly, fecal pellets were weighed and diluted to 1 g/mL in PBS. After homogenization by vortexing, fecal samples were then centrifuged at 4,000 rpm for 10 min. Supernatants were stored at −20° C. prior to IgA measurement. Sera samples were collected two weeks after prime and second boost vaccination to monitor changes in antibody levels. Sera was collected via retro-orbital bleeding and incubated at room temperature for 30 minutes to allow clotting. Sera was separated from whole blood by centrifugation at 10,000 rpm for 10 min. Supernatants were collected and stored at −80° C. prior to enzyme-linked immunosorbent assay (ELISA).

Infection.

Two weeks after the second boost, all mice were challenged with a dose of $5\times10^9$ CFU of streptomycin resistant *E. coli* O157:H7 strain 86-24 via gavage (400 μL). Food was restricted 12 h before infection but was administered ad libitum throughout the remainder of the study. Two hours prior to challenge, mice were injected intraperitoneally with cimetidine (50 mg/kg, Sigma) to reduce stomach acidity. Fecal samples were collected daily for seven days to assess bacterial shedding. Fecal pellets were homogenized in phosphate-buffered saline (PBS), serially diluted, and plated on MacConkey agar plates containing streptomycin (25 μg/mL) and incubated at 37° C. To enumerate bacterial colonization in gastrointestinal tract, mice were euthanized, and ceca and large intestines were removed. Organs were homogenized in 1 mL PBS, serially diluted and plated on MacConkey agar containing streptomycin.

ELISA.

Total IgG and IgA responses were determined using Ready-set-Go!™ ELISA kits (EBioscience) and were performed according to manufacturer's instructions. To determine immunoglobulin levels, polystyrene 96-well high-binding ELISA plates (Nunc, Denmark) were coated overnight with capture IgG or IgA antibody at 4° C. The plates were washed 2× with PBS containing 0.05% Tween 20 (PBS-T) prior to blocking in 2× Assay Buffer. For IgG, the serum samples were diluted (1:1,000 and 1:10,000) in 1× Assay Buffer. Similarly, for IgA levels, samples were diluted (1:2 and 1:4) in 1× Assay Buffer. Following incubation, horseradish peroxidase (HRP)-conjugated goat anti-mouse IgG, or goat anti-mouse IgA was diluted in 1× Assay Buffer (1:250) and added to ELISA plates to determine IgG and IgA concentration, respectively. Plates were incubated with agitation for 3 hours at room temperature, followed by washing. A total of 100 μL of tetramethylbenzidine (TMB) was added to each well and incubated at room temperature for 15 minutes. The reaction was stopped using 100 μL of 2N $H_2SO_4$ and plate was read at 450 nm (Biotech Microplate Spectrophotometer).

Bacterial Adhesion Assay.

Caco-2 cells (ATCC® HTB-37™) were maintained at 37° C. with 5% $CO_2$ in complete HTB-37 medium. Complete HTB-37 media consisted of Eagle's Minimum Essential Medium (EMEM, GIBCO) supplemented with 2 mM glutamine, 1 mM sodium pyruvate, 1× non-essential amino acids, penicillin-streptomycin (100 U/ml, 100 μg/ml), and 10% fetal bovine serum. For adhesion assays, 12-well plates were seeded with $10^5$ cells per well and incubated as described above to achieve 80% confluence. Approximately 1 h prior to infection, the monolayer was washed twice with 1 ml PBS prior to addition of 1 ml medium containing no supplements. Fresh bacterial culture of *E. coli* O157:H7 strain EDL933 was grown in LB overnight at 37° C. prior to infection. Bacterial culture was diluted in LB (1:100) and incubated at 37° C., shacking, until culture reached an $OD_{600}$ of 1.0. Culture was pelleted at 5000×g for 5 minutes, resuspended in PBS ($Ca^{2+}$ and $Mg^{2+}$ free), and plated for input bacterial load. Remaining bacteria was incubated with immune or naïve sera (5% and 10%) for 45 minutes at 37° C. with agitation. At this time, media was removed and replaced with 1 ml fresh media containing $10^7$ bacterial cells (multiplicity of infection [MOI], 100). Inoculated monolayers were incubated for 3 h at 37° C. with 5% $CO_2$. After incubation, cells were washed three times with PBS prior to addition of 200 μl of 0.1% Triton X-100 in PBS. Wells were incubated at 37° C. until cell monolayer detached from the plate. Monolayers were homogenized by pipetting, then samples were serially diluted and plated onto LB agar. The percentage of bacteria recovered was calculated as the number of CFU/ml recovered divided by the input CFU/ml to account for slight variances in input between groups.

Statistical Analysis.

Statistical significance between control and vaccinated groups was assessed using GraphPad software. One-way analysis of variance (ANOVA) and Student t test were used to analyze the data for colonization and antibody response, respectively. Adhesion assay experiments were repeated in triplicate. Bacteria recovered were normalized to the mean percentage of the bacteria inoculated and the groups were compared using one-way ANOVA followed by Kruskal-Wallis posthoc test. P-values <0.05 were considered significant.

The invention claimed is:

1. A method for reducing Enterohemorrhagic *Escherichia coli* (EHEC) colonization of the large intestine in a subject comprising providing to a subject a therapeutic amount of a polypeptide having an amino acid sequence of SEQ ID NO:22.

2. The method of claim 1, wherein the polypeptide is provided by administering an expression vector that encodes the polypeptide.

3. The method of claim 1, wherein the subject is bovine.

4. The method of claim 1, wherein the subject is human.

5. The method of claim 1, wherein the subject is administered a polypeptide having an amino acid sequence of SEQ ID NO:22.

6. The method of claim 2, wherein the expression vector is administered intranasally.

7. The method of claim 1, wherein the polypeptide is provided as a priming dose followed by at least two boosting doses.

* * * * *

SEQUENCE LISTING

```
<160> NUMBER OF SEQ ID NOS: 23

<210> SEQ ID NO 1
<211> LENGTH: 199
<212> TYPE: PRT
<213> ORGANISM: Escherichia coli

<400> SEQUENCE: 1

Met Arg Lys Leu Tyr Ala Ala Ile Leu Ser Ala Ala Ile Cys Leu Ala
1               5                   10                  15

Val Ser Gly Ala Pro Ala Trp Ala Ser Glu Gln Gln Ala Thr Leu Ser
            20                  25                  30

Ala Gly Tyr Leu His Ala Arg Thr Ser Ala Pro Gly Ser Asp Asn Leu
        35                  40                  45

Asn Gly Ile Asn Val Lys Tyr Arg Tyr Glu Phe Thr Asp Thr Leu Gly
    50                  55                  60

Leu Val Thr Ser Phe Ser Tyr Ala Gly Asp Lys Asn Arg Gln Leu Thr
65                  70                  75                  80

Arg Tyr Ser Asp Thr Arg Trp His Glu Asp Ser Val Arg Asn Arg Trp
                85                  90                  95

Phe Ser Val Met Ala Gly Pro Ser Val Arg Val Asn Glu Trp Phe Ser
            100                 105                 110

Ala Tyr Ala Met Ala Gly Val Ala Tyr Ser Arg Val Ser Thr Phe Ser
        115                 120                 125

Gly Asp Tyr Leu Arg Val Thr Asp Asn Lys Gly Lys Thr His Asp Val
    130                 135                 140

Leu Thr Gly Ser Asp Asp Gly Arg His Ser Asn Thr Ser Leu Ala Trp
145                 150                 155                 160

Gly Ala Gly Val Gln Phe Asn Pro Thr Glu Ser Val Ala Ile Asp Ile
                165                 170                 175

Ala Tyr Glu Gly Ser Gly Ser Gly Asp Trp Arg Thr Asp Gly Phe Ile
            180                 185                 190

Val Gly Val Gly Tyr Lys Phe
        195


<210> SEQ ID NO 2
<211> LENGTH: 186
<212> TYPE: PRT
<213> ORGANISM: Escherichia coli

<400> SEQUENCE: 2

Met Phe Ser Thr Phe Lys Lys Ala Ala Leu Leu Ala Ala Ile Ala Leu
1               5                   10                  15

Pro Phe Ser Thr Met Ala Ala Pro Thr Val Thr Phe Gln Gly Glu Val
            20                  25                  30

Thr Asp Gln Thr Cys Ser Val Asn Ile Asn Gly Gln Thr Asn Ser Val
        35                  40                  45

Val Leu Met Pro Thr Val Ala Met Ala Asp Phe Gly Ala Thr Leu Ala
    50                  55                  60

Asp Gly Gln Ser Ala Gly Gln Thr Pro Phe Thr Val Ser Val Ser Asn
65                  70                  75                  80

Cys Gln Ala Pro Thr Gly Ala Asp Gln Ala Ile Asn Thr Thr Phe Leu
                85                  90                  95
```

```
Gly Tyr Asp Val Asp Ala Ser Thr Gly Val Met Gly Asn Arg Asp Thr
            100                 105                 110

Ser Ser Asp Ala Ala Lys Gly Phe Gly Ile Gln Leu Met Asp Ser Ser
        115                 120                 125

Thr Ser Gly Asn Pro Val Thr Leu Ala Gly Ala Thr Asn Val Pro Gly
    130                 135                 140

Leu Thr Leu Lys Val Gly Asp Thr Glu Ala Ser Tyr Asp Phe Gly Ala
145                 150                 155                 160

Arg Tyr Phe Val Ile Asp Ser Ala Ala Ala Thr Ala Gly Lys Ile Thr
                165                 170                 175

Ala Val Ala Glu Tyr Thr Leu Ser Tyr Leu
            180                 185


<210> SEQ ID NO 3
<211> LENGTH: 512
<212> TYPE: PRT
<213> ORGANISM: Escherichia coli

<400> SEQUENCE: 3

Met Lys Lys Ile Ser Phe Phe Ile Phe Thr Ala Leu Phe Cys Cys Ser
1               5                   10                  15

Ala Gln Ala Ala Pro Ser Ser Leu Glu Lys Arg Leu Gly Lys Ser Glu
            20                  25                  30

Tyr Phe Ile Ile Thr Lys Ser Ser Pro Val Arg Ala Ile Leu Asn Asp
        35                  40                  45

Phe Ala Ala Asn Tyr Ser Ile Pro Val Phe Ile Ser Ser Ser Val Asn
    50                  55                  60

Asp Asp Phe Ser Gly Glu Ile Lys Asn Glu Lys Pro Val Lys Val Leu
65                  70                  75                  80

Glu Lys Leu Ser Lys Leu Tyr His Leu Thr Trp Tyr Tyr Asp Glu Asn
                85                  90                  95

Ile Leu Tyr Ile Tyr Lys Thr Asn Glu Ile Ser Arg Ser Ile Ile Thr
            100                 105                 110

Pro Thr Tyr Leu Asp Ile Asp Ser Leu Leu Lys Tyr Leu Ser Asp Thr
        115                 120                 125

Ile Ser Val Asn Lys Asn Ser Cys Asn Val Arg Lys Ile Thr Thr Phe
    130                 135                 140

Asn Ser Ile Glu Val Arg Gly Val Pro Glu Cys Ile Lys Tyr Ile Thr
145                 150                 155                 160

Ser Leu Ser Glu Ser Leu Asp Lys Glu Ala Gln Ser Lys Ala Lys Asn
                165                 170                 175

Lys Asp Val Val Lys Val Phe Lys Leu Asn Tyr Ala Ser Ala Thr Asp
            180                 185                 190

Ile Thr Tyr Lys Tyr Arg Asp Gln Asn Val Val Val Pro Gly Val Val
        195                 200                 205

Ser Ile Leu Lys Thr Met Ala Ser Asn Gly Ser Leu Pro Ser Thr Gly
    210                 215                 220

Lys Gly Ala Val Glu Arg Ser Gly Asn Leu Phe Asp Asn Ser Val Thr
225                 230                 235                 240

Ile Ser Ala Asp Pro Arg Leu Asn Ala Val Val Val Lys Asp Arg Glu
                245                 250                 255

Ile Thr Met Asp Ile Tyr Gln Gln Leu Ile Ser Glu Leu Asp Ile Glu
            260                 265                 270

Gln Arg Gln Ile Glu Ile Ser Val Ser Ile Ile Asp Val Asp Ala Asn
```

-continued

```
        275                 280                 285

Asp Leu Gln Gln Leu Gly Val Asn Trp Ser Gly Thr Leu Asn Ala Gly
    290                 295                 300

Gln Gly Thr Ile Ala Phe Asn Ser Ser Thr Ala Gln Ala Asn Ile Ser
305                 310                 315                 320

Ser Ser Val Ile Ser Asn Ala Ser Asn Phe Met Ile Arg Val Asn Ala
                325                 330                 335

Leu Gln Gln Asn Ser Lys Ala Lys Ile Leu Ser Gln Pro Ser Ile Ile
            340                 345                 350

Thr Leu Asn Asn Met Gln Ala Ile Leu Asp Lys Asn Val Thr Phe Tyr
        355                 360                 365

Thr Lys Val Ser Gly Glu Lys Val Ala Ser Leu Glu Ser Ile Thr Ser
    370                 375                 380

Gly Thr Leu Leu Arg Val Thr Pro Arg Ile Leu Asp Asp Ser Ser Asn
385                 390                 395                 400

Ser Leu Thr Gly Lys Arg Arg Glu Arg Val Arg Leu Leu Leu Asp Ile
                405                 410                 415

Gln Asp Gly Asn Gln Ser Thr Asn Gln Ser Asn Ala Gln Asp Ala Ser
            420                 425                 430

Ser Thr Leu Pro Glu Val Gln Asn Ser Glu Met Thr Thr Glu Ala Thr
        435                 440                 445

Leu Ser Ala Gly Glu Ser Leu Leu Leu Gly Gly Phe Ile Gln Asp Lys
    450                 455                 460

Glu Ser Ser Ser Lys Asp Gly Ile Pro Leu Leu Ser Asp Ile Pro Val
465                 470                 475                 480

Ile Gly Ser Leu Phe Ser Ser Thr Val Lys Gln Lys His Ser Val Val
                485                 490                 495

Arg Leu Phe Leu Ile Lys Ala Thr Pro Ile Lys Ser Ala Ser Ser Glu
            500                 505                 510
```

<210> SEQ ID NO 4
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 4
accaagctta ccatggtttc tactttcaaa aaagcag 37

<210> SEQ ID NO 5
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 5
accctcgagt agaggtagct cagggtgtat tct 33

<210> SEQ ID NO 6
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 6
attaagctta ccatgggtaa actttatgcc gccattttg 39

-continued

<210> SEQ ID NO 7
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 7
attctcgagt caatgatgat gatgatgatg gaacttataa ccgacaccca c 51

<210> SEQ ID NO 8
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 8
accaagctta ccatggaccg cgaaataacg atggat 36

<210> SEQ ID NO 9
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 9
accctcgagt tattcgctag atgcagattt tatc 34

<210> SEQ ID NO 10
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 10
attaagctta ccatgggtgg ttcaagactg gctgataatc 40

<210> SEQ ID NO 11
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 11
attctcgagt taaaaacgat aaccaactcc aac 33

<210> SEQ ID NO 12
<211> LENGTH: 47
<212> TYPE: DNA
<213> ORGANISM: Artificial Sequence
<220> FEATURE:
<223> OTHER INFORMATION: synthetic oligonucletoide

<400> SEQUENCE: 12
attaagctta ccatggcttt ttcttttttt tctacaaaac ccatacc 47

<210> SEQ ID NO 13
<211> LENGTH: 31
<212> TYPE: DNA
<213> ORGANISM: Artificial Sequence
<220> FEATURE:

-continued

<223> OTHER INFORMATION: synthetic oligonucleotide

<400> SEQUENCE: 13
attctcgagt tatccgcccg caccattaac c 31

<210> SEQ ID NO 14
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 14
accaagctta ccatgggtaa agtttgtgca gcaa 34

<210> SEQ ID NO 15
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 15
accctcgagt caaaatttat aaccgacacc cac 33

<210> SEQ ID NO 16
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 16
attaagctta ccatggatac tattgataat actcaag 37

<210> SEQ ID NO 17
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 17
attctcgagt caatgatgat gatgatgatg cccagctaag cgacccgatt g 51

<210> SEQ ID NO 18
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 18
accaagctta ccatggccga tgccgttaac ggctc 35

<210> SEQ ID NO 19
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 19
ttatctagac tcgagttact cggcgttcgc aatggtg 37

<210> SEQ ID NO 20
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 20
accaagctta ccatggaact gctcggtgca ttgtct 36

<210> SEQ ID NO 21
<211> LENGTH: 37
<212> TYPE: DNA
<213> ORGANISM: Artificial Sequence
<220> FEATURE:
<223> OTHER INFORMATION: synthetic oligonucletodie

<400> SEQUENCE: 21
ttatctagac tcgagttagc cggaaccaat cgcgacg 37

<210> SEQ ID NO 22
<211> LENGTH: 244
<212> TYPE: PRT
<213> ORGANISM: Escherichia coli

<400> SEQUENCE: 22

Met Lys Ser Ile Ala Thr Leu Val Val Cys Ala Ile Ser Gly Ile Ala
1 5 10 15

Cys Val Asn Leu Ser Ala His Ala Ala Glu Gly Glu His Thr Ile Ser
20 25 30

Leu Gly Tyr Ala His Phe Gln Phe Pro Gly Leu Lys Asp Phe Val Lys
35 40 45

Asp Ala Thr Ala His Asn Arg Glu Thr Phe Ser His Phe Val Asn Arg
50 55 60

Asn Tyr Phe Ser Ser Leu Gly Glu Tyr Thr Asp Gly Arg Val Ser Gly
65 70 75 80

Tyr Glu Gly Lys Asp Lys Asn Pro Gln Gly Ile Asn Ile Arg Tyr Arg
85 90 95

Tyr Glu Ile Thr Asp Asp Phe Gly Val Ile Thr Ser Phe Thr Trp Thr
100 105 110

Arg Ser Leu Thr Asn Ser Gln Thr Phe Ile Asp Val Gln Ser Ala Asp
115 120 125

His Thr Arg Lys Ile Lys Asn Pro Ala Ala Ser Ala Arg Thr Asp Ile
130 135 140

Arg Ala Asn Tyr Trp Ser Leu Leu Ala Gly Pro Ser Trp Arg Val Asn
145 150 155 160

Gln Tyr Met Ser Leu Tyr Ala Met Ala Gly Met Gly Val Ala Lys Val
165 170 175

Ser Ala Asp Leu Lys Ile Lys Asp Asn Ile Asn Ser Ser Gly Gly Phe
180 185 190

Ser Glu Ser Asn Ser Thr Lys Lys Thr Ser Leu Ala Trp Ala Ala Gly
195 200 205

Ala Gln Phe Asn Leu Asn Glu Ser Val Thr Leu Asp Val Ala Tyr Glu
210 215 220

Gly Ser Gly Ser Gly Asp Trp Arg Thr Ser Gly Val Thr Ala Gly Ile
225 230 235 240

Gly Leu Lys Phe

-continued

```
<210> SEQ ID NO 23
<211> LENGTH: 190
<212> TYPE: PRT
<213> ORGANISM: Escherichia coli

<400> SEQUENCE: 23

Met Lys Lys His Ile Lys Asn Leu Phe Leu Leu Ala Ala Ile Cys Leu
1               5                   10                  15

Thr Val Ala Cys Lys Glu Gln Leu Tyr Thr Gly Leu Thr Glu Lys Glu
            20                  25                  30

Ala Asn Gln Met Gln Ala Leu Leu Leu Ser Asn Asp Val Asn Val Ser
        35                  40                  45

Lys Glu Met Asp Lys Ser Gly Asn Met Thr Leu Ser Val Glu Lys Glu
    50                  55                  60

Asp Phe Val Arg Ala Ile Thr Ile Leu Asn Asn Asn Gly Phe Pro Lys
65                  70                  75                  80

Lys Lys Phe Ala Asp Ile Glu Val Ile Phe Pro Pro Ser Gln Leu Val
                85                  90                  95

Ala Ser Pro Ser Gln Glu Asn Ala Lys Ile Asn Tyr Leu Lys Glu Gln
            100                 105                 110

Asp Ile Glu Arg Leu Leu Ser Lys Ile Pro Gly Val Ile Asp Cys Ser
        115                 120                 125

Val Ser Leu Asn Val Asn Asn Asn Glu Ser Gln Pro Ser Ser Ala Ala
    130                 135                 140

Val Leu Val Ile Ser Ser Pro Glu Val Asn Leu Ala Pro Ser Val Ile
145                 150                 155                 160

Gln Ile Lys Asn Leu Val Lys Asn Ser Val Asp Asp Leu Lys Leu Glu
                165                 170                 175

Asn Ile Ser Val Val Ile Lys Ser Ser Ser Gly Gln Asp Gly
            180                 185                 190
```